(12) United States Patent
Chantz et al.

(10) Patent No.: US 11,719,681 B2
(45) Date of Patent: Aug. 8, 2023

(54) CAPTURING AND ANALYZING DATA IN A DRONE ENABLED ENVIRONMENT FOR ECOLOGICAL DECISION MAKING

(71) Applicant: International Business Machines Corporation, Armonk, NY (US)

(72) Inventors: Hyman David Chantz, Scarsdale, NY (US); Doga Tav, Fredericton (CA)

(73) Assignee: International Business Machines Corporation, Armonk, NY (US)

( * ) Notice: Subject to any disclaimer, the term of this patent is extended or adjusted under 35 U.S.C. 154(b) by 355 days.

(21) Appl. No.: 17/085,450

(22) Filed: Oct. 30, 2020

(65) Prior Publication Data

US 2022/0137023 A1 May 5, 2022

(51) Int. Cl.
*G01N 33/24* (2006.01)
*G01N 27/04* (2006.01)
(Continued)

(52) U.S. Cl.
CPC ........... *G01N 33/24* (2013.01); *A01B 79/005* (2013.01); *B64C 39/024* (2013.01);
(Continued)

(58) Field of Classification Search
CPC ................. G01N 33/24; G01N 27/041; G01N 2033/245; A01B 79/005; B64C 39/024; B64C 2201/12; G05D 1/0094
See application file for complete search history.

(56) References Cited

U.S. PATENT DOCUMENTS 3,326,049 A 6/1967 Eley
6,484,652 B1 * 11/2002 Colburn, Jr. ......... A01C 21/007
47/1.3
(Continued)

FOREIGN PATENT DOCUMENTS

BR 102018012008 A2 * 12/2019
CN 104848893 A 8/2015
(Continued)

OTHER PUBLICATIONS

Dabas et al., Comparison of instruments for geoelectrical soil mapping at the field scale, Near Surface Geophysics, Jun. 2009, 7(3): 179-190 (Year: 2009).*
(Continued)

*Primary Examiner* — Kyle R Quigley
*Assistant Examiner* — Xiuqin Sun
(74) *Attorney, Agent, or Firm* — Michael A. Petrocelli

(57) ABSTRACT

Capturing data in a drone enabled environmental for testing soil and ecological decision making includes initiating, using a computer, collection of data from multiple sources using a drone. The data includes information about soil at a specified soil location, in response to the drone flying over air space of a physical or geographical location respective to the soil location and/or landing at the soil location. Soil data is received, as part of the data, from the drone in response to testing the soil. The testing of the soil can include conducting a ground conductivity test using two or more probes coupled to respective landing pads of the drone, and positioning the drone over the soil location such that the two or more probes contact the soil. The data is analyzed to determine a best location for seeding and growing a plant in the soil.

20 Claims, 9 Drawing Sheets

(51) Int. Cl.
  *G05D 1/00* (2006.01)
  *B64C 39/02* (2023.01)
  *A01B 79/00* (2006.01)
  *B64U 101/00* (2023.01)
(52) U.S. Cl.
  CPC ......... *G01N 27/041* (2013.01); *G05D 1/0094* (2013.01); *B64U 2101/00* (2023.01); *G01N 2033/245* (2013.01)

(56) References Cited

U.S. PATENT DOCUMENTS

| | | | |
|---|---|---|---|
| 6,963,205 | B2 | 11/2005 | Lundstrom |
| 10,125,464 | B2 | 11/2018 | Berney, IV |
| 10,985,539 | B1 * | 4/2021 | Thomas ............... B64C 39/02 |
| 2015/0070188 | A1 | 3/2015 | Aramburu |
| 2018/0314949 | A1 | 11/2018 | Bender |
| 2019/0101505 | A1 | 4/2019 | Liu |

FOREIGN PATENT DOCUMENTS

| | | |
|---|---|---|
| EP | 3545760 A1 | 10/2019 |
| KR | 101845395 B1 | 4/2018 |
| KR | 101967584 B1 | 4/2019 |
| WO | 2013131882 A2 | 9/2013 |
| WO | 2016110832 A1 | 7/2016 |

OTHER PUBLICATIONS

"14 CFR Part 107—Small Unmanned Aircraft Systems", Legal Information Institute, LII > Electronic Code of Federal Regulations (e-CFR) > Title 14. Aeronautics and Space > Chapter I. Federal Aviation Administration, Department of Transportation > Subchapter F. Air Traffic and General Operating Rules > Part 107. Small Unmanned Aircraft Systems, 1 page, <https://www.law.cornell.edu/cfr/text/14/part-107>.
"FAA Drone Registry Tops One Million", US Department of Transportation, Last printed Oct. 28, 2020, 2 pages, <https://www.transportation.gov/briefing-room/faa-drone-registry-tops-one-million>.
"HD Soil Sampling", Integrated Ag Services, last printed Oct. 28, 2020, 2 pages, <https://integratedag.net/services/high-density-automated-precision-soil-sampling>.
"How to Take an Accurate Soil Sample", Pennington Seed, Inc., © 2019 Pennington Seed, Inc., 5 pages, <https://www.pennington.com/all-products/grass-seed/resources/how-to-take-an-accurate-soil-sample>.
"Soil Sampling", Mosaic, Nutrient Management, last printed Oct. 28, 2020, 16 pages, <https://www.cropnutrition.com/nutrient-management/soil-sampling>.
Calma, Justine, "Dirty air cuts back California crops", The Verge, Mar. 16, 2020, 3 pages, <https://www.theverge.com/2020/3/16/21181725/air-pollution-california-crops-agriculture-1-billion>.
Chantz, et al., "Capturing and Analyzing Data in a Drone Enabled Environment for Ecological Decision Making", U.S. Appl. No. 17/085,489, filed Oct. 30, 2020.
Chantz, Hy, "Using Blockchain to Address Drone Cybersecurity", Security Intelligence, Aug. 25, 2016, 5 pages, <https://securityintelligence.com/using-blockchain-to-address-drone-cybersecurity/>.
Chantz, Hy, "Weather, wither, whether: How blockchain enables precision agriculture", Blockchain Pulse: IBM Blockchain Blog, May 30, 2018, 3 pages, <https://www.ibm.com/blogs/blockchain/2018/05/weather-wither-whether-how-blockchain-enables-precision-agriculture/>.
Cohen, Nancy, "Forget pills and pizza. These drones are landing, drilling holes, and taking off again", Tech Xplore, Jan. 10, 2019, 4 pages, <https://techxplore.com/news/2019-01-pills-pizza-drones-drilling-holes.html>.
Gilbert, Tony, "Why is soil conductivity mapping so important to farmers?", Queensland Drones, May 26, 2018, 5 pages, <https://qlddrones.com.au/why-is-soil-conductivity-mapping-so-important-to-farmers/>.
Hu, et al., "Quantitative Estimation of Soil Salinity Using UAV-Borne Hyperspectral and Satellite Multispectral Images", Remote Sensing, 2019, 11, 736, 16 pages.
Huuskonen, et al. ,"Soil sampling with drones and augmented reality in precision agriculture", Computers and Electronics in Agriculture, vol. 154, Nov. 2018, pp. 25-35, <https://www.sciencedirect.com/science/article/pii/S0168169918301650?via%3Dihub>.
Liptak, Andrew, "The FAA says the commercial drone market could triple in size by 2023", The Verge, May 4, 2019, 2 pages, <https://www.theverge.com/2019/5/4/18529241/faa-annual-aviation-report-hobby-commercial-drones-prediction-2023>.
List of IBM Patents or Patent Applications Treated as Related. Filed Herewith. 2 pages.
Mell et al., "The NIST Definition of Cloud Computing", National Institute of Standards and Technology, Special Publication 800-145, Sep. 2011, 7 pages.
Speeds, Joe, "#WatsonIoT is growing", Twitter, Jul. 26, 2017, 1 page, <https://twitter.com/JoeSpeeds/status/890164885451137025>.
Sudduth, et al, "Accuracy issues in electromagnetic induction sensing of soil electrical conductivity for precision agriculture", Computers and Electronics in Agriculture, vol. 31, No. 3, May 2001, pp. 239-264.
"Crop Nutrition From The Mosaic Company", Mosaic, last printed Oct. 23, 2020, 5 pages, <https://www.cropnutrition.com/>.
"Hands Free Hectare", last printed Oct. 23, 2020, 3 pages, <https://www.handsfreehectare.com/>.

* cited by examiner

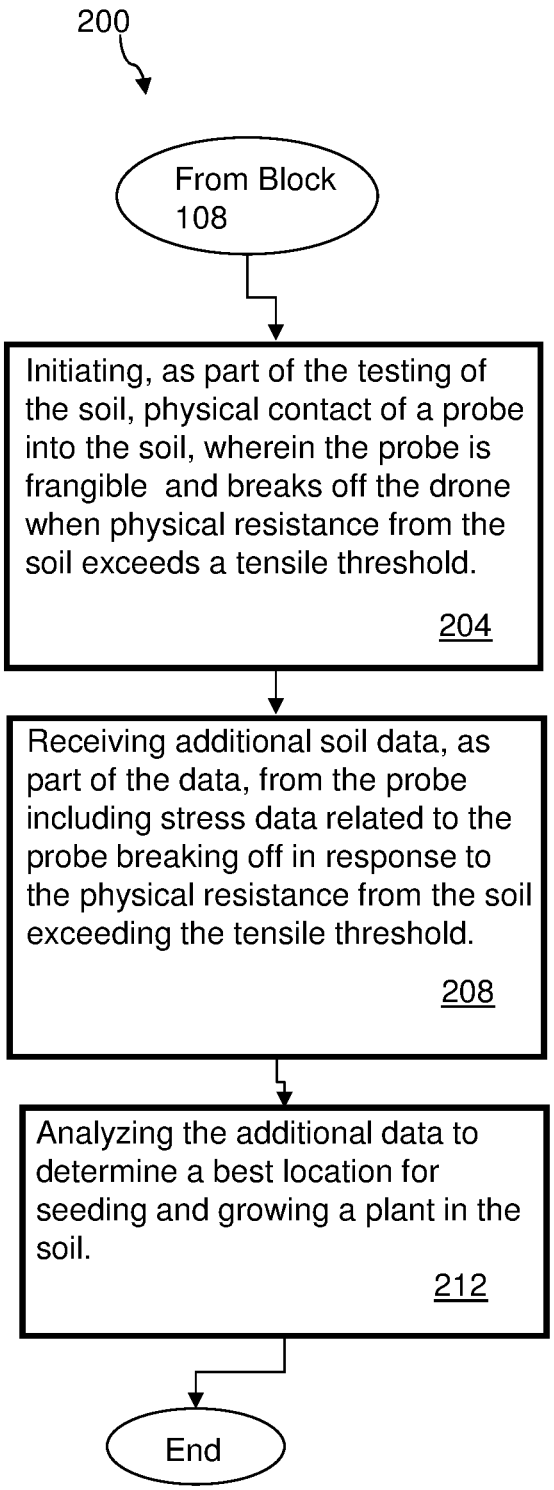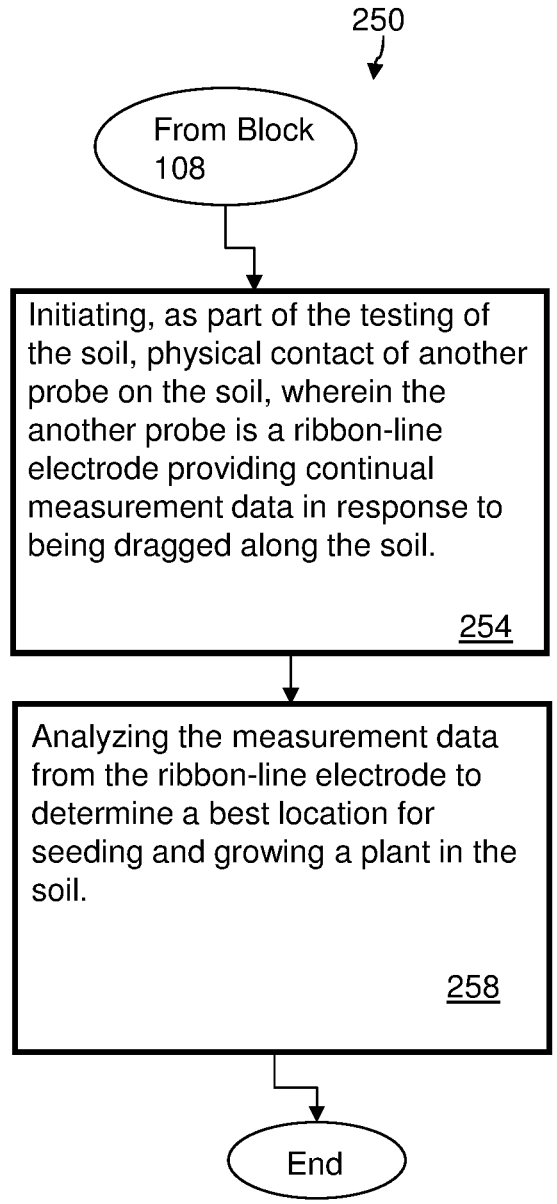
FIG. 3A
FIG. 3B

US 11,719,681 B2

CAPTURING AND ANALYZING DATA IN A DRONE ENABLED ENVIRONMENT FOR ECOLOGICAL DECISION MAKING

BACKGROUND

The present disclosure relates to computerized capturing of data in a drone enabled environment for ecological decisions, and more specifically, related to controlling a drone to conduct soil tests.

Interest in improving agriculture for farms, whether small or large, can include soil evaluation including capturing soil samples and conducting measurements and tests on the soil.

Drones, as a mobile platform, can be used for soil analysis (e.g., moisture analysis) using soil conductivity. Also, drones can be used for implementing drill-like elements for obtaining soil samples and/or deploying soil sensors.

SUMMARY

The present disclosure recognizes the shortcomings and problems associated with current techniques for capturing data in using a drone for testing and/or measuring soil and ecological decision making.

The present invention recognizes the need for improvements in soil analysis (e.g., moisture analysis) using soil conductivity testing and measurements and/or soil sensors. In one embodiment, the present invention can use four probes coupled to four pads of a drone for performing ground conductivity tests. In other embodiments, the present invention can use frangible probes, and/or ribbon-line electrodes (along with consideration of a stress threshold which can include considerations of tensile thresholds and compressive thresholds) for performing drone-based tests and capturing soil measurements and data.

The present invention can use AI (Artificial Intelligence) to leverage the capabilities of one or more drones, in correlating soil moisture with actual growing conditions, via multispectral optical, radio, and acoustical passive imaging, and by correlating these with agriculture sampling, inputs and outputs. Measurements such as radio signal reflectivity to soil moisture using the present invention can use comprehensive multi-spectral agricultural approach using drones and AI. Embodiments of the present invention can aid in solving agricultural problems and mitigating agricultural issues, such as ground-level air pollution as an inhibitor for crops, by providing soil measurements and data.

In an aspect according to the present invention, a computer-implemented method for capturing data in a drone enabled environmental for testing soil and ecological decision making includes initiating, using a computer, collection of data from multiple sources using a drone. The data regarding information about soil at a specified soil location, in response to the drone flying over air space of a physical or geographical location respective to the soil location and/or landing at the soil location. The method includes receiving, using the computer, soil data, as part of the data, from the drone in response to testing the soil, the testing of the soil including conducting a ground conductivity test using two or more probes coupled to respective landing pads of the drone, and positioning the drone over the soil location such that the two or more probes contact the soil. The method includes analyzing the data to determine a best location for seeding and growing a plant in the soil.

In a related aspect, the ground conductivity test uses four probes coupled to four landing pads of the drone, and the method further comprises initiating electrical measurements using the four probes including a multiplicity of resistance measurements using a set of possible combinations of the four probes; and the method receiving, using the computer, the electrical measurements from the drone as part of the soil data.

In a related aspect, the method includes initiating, as part of the testing of the soil, physical contact of a probe into the soil, wherein the probe is frangible and breaks off the drone when physical resistance from the soil exceeds a stress threshold. The method includes receiving additional soil data, as part of the data, from the probe including stress data related to the probe breaking off in response to the physical resistance from the soil exceeding the stress threshold; and analyzing the additional data to determine a best location for seeding and growing a plant in the soil.

In a related aspect, the method further including initiating, as part of the testing of the soil, physical contact of another probe on the soil, wherein the another probe is a ribbon-line electrode providing continual measurement data in response to being dragged along the soil; and analyzing the measurement data from the ribbon-line electrode to determine a best location for seeding and growing a plant in the soil.

In a related aspect, the method further including receiving additional soil data, as part of the data, from the another probe including stress data related to the another probe breaking off in response to physical resistance from the soil exceeding a stress threshold; and analyzing the additional soil data to determine a best location for seeding and growing a plant in the soil, in response to the receiving of the additional soil data.

In a related aspect, the method further including initiating, as part of the testing of the soil, drilling into the soil, using a mini drill coupled to the drone; receiving soil samples from the drilling when the drone returns to a home base; generating soil sample data, as part of the data, from the soil samples; and analyzing the soil sample data to determine a best location for seeding and growing a plant in the soil.

In a related aspect, wherein the conducting of the ground conductivity test can use four probes coupled to respective landing pads of the drone, and the drone is positioned over the soil location such that the four probes contact the soil; and the method further comprising: initiating testing of the soil using resistance measurements between the four probes; receiving, using the computer, the soil data, as part of the data, including the resistance measurements from the drone in response to the testing the soil using the four probes; and analyzing the data to determine a best location for seeding and growing a plant in the soil.

In a related aspect the testing of the soil can use the resistance measurements between the four probes includes determining an optimum resistance using vector algebra.

In a related aspect wherein the testing of the soil can use the resistance measurements between the four probes includes using a mathematical combination of the four probes.

In another aspect, a system uses a computer for capturing data in a drone enabled environmental for testing soil and ecological decision making, which comprises: a computer system comprising; a computer processor, a computer-readable storage medium, and program instructions stored on the computer-readable storage medium being executable by the processor, to cause the computer system to perform the following functions to; initiate, using a computer, collection of data from multiple sources using a drone, the data regarding information about soil at a specified soil location, in response to the drone flying over air space of a physical or geographical location respective to the soil location and/or landing at the soil location; receive, using the computer, soil data, as part of the data, from the drone in response to testing the soil, the testing of the soil including conducting a ground conductivity test using two or more probes coupled to respective landing pads of the drone, and position the drone over the soil location such that the two or more probes contact the soil; and analyze the data to determine a best location for seeding and growing a plant in the soil.

In a related aspect, the ground conductivity test uses four probes coupled to four landing pads of the drone, and the system further comprising: initiating electrical measurements using the four probes including a multiplicity of resistance measurements using a set of possible combinations of the four probes; and receiving, using the computer, the electrical measurements from the drone as part of the soil data.

In a related aspect, the system further includes initiate, as part of the testing of the soil, physical contact of a probe into the soil, wherein the probe is frangible and breaks off the drone when physical resistance from the soil exceeds a stress threshold; receive additional soil data, as part of the data, from the probe including stress data related to the probe breaking off in response to the physical resistance from the soil exceeding the stress threshold; and analyze the additional data to determine a best location for seeding and growing a plant in the soil.

In a related aspect, the system further includes initiating, as part of the testing of the soil, physical contact of another probe on the soil, wherein the another probe is a ribbon-line electrode providing continual measurement data in response to being dragged along the soil; and analyzing the measurement data from the ribbon-line electrode to determine a best location for seeding and growing a plant in the soil.

In a related aspect, the system further includes receiving additional soil data, as part of the data, from the another probe including stress data related to the another probe breaking off in response to physical resistance from the soil exceeding a stress threshold; and analyzing the additional soil data to determine a best location for seeding and growing a plant in the soil, in response to the receiving of the additional soil data.

In a related aspect, the system further including initiating, as part of the testing of the soil, drilling into the soil, using a mini drill coupled to the drone; receiving soil samples from the drilling when the drone returns to a home base; generating soil sample data, as part of the data, from the soil samples; and analyzing the soil sample data to determine a best location for seeding and growing a plant in the soil.

In a related aspect, the conducting of the ground conductivity test uses four probes coupled to respective landing pads of the drone, and the drone is positioned over the soil location such that the four probes contact the soil; and the system further comprising: initiating testing of the soil using resistance measurements between the four probes; receiving, using the computer, the soil data, as part of the data, including the resistance measurements from the drone in response to the testing the soil using the four probes; analyzing the data to determine a best location for seeding and growing a plant in the soil.

In a related aspect, the testing of the soil uses the resistance measurements between the four probes includes determining an optimum resistance using vector algebra.

In a related aspect, the testing of the soil using the resistance measurements between the four probes includes using a mathematical combination of the four probes.

In another aspect, a computer program product for capturing data in a drone enabled environmental for testing soil and ecological decision making, the computer program product comprising a computer readable storage medium having program instructions embodied therewith. The program instructions executable by a computer to cause the computer to perform functions, by the computer, comprising the functions to: initiate, using a computer, collection of data from multiple sources using a drone, the data regarding information about soil at a specified soil location, in response to the drone flying over air space of a physical or geographical location respective to the soil location and/or landing at the soil location; receive, using the computer, soil data, as part of the data, from the drone in response to testing the soil, the testing of the soil including conducting a ground conductivity test using two or more probes coupled to respective landing pads of the drone, and position the drone over the soil location such that the two or more probes contact the soil; and analyze the data to determine a best location for seeding and growing a plant in the soil.

In a related aspect, the ground conductivity test uses four probes coupled to four landing pads of the drone, and the computer program product further comprising: initiating electrical measurements using the four probes including a multiplicity of resistance measurements using a set of possible combinations of the four probes; and receiving, using the computer, the electrical measurements from the drone as part of the soil data.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. The drawings are discussed forthwith below.

FIG. 3A is a flow chart illustrating another method, implemented using the system shown in FIG. 1, and continuing from the flow chart shown in FIG. 2, for capturing data in a drone enabled environmental for testing soil and ecological decision making, according to an embodiment of the present disclosure.

FIG. 3B is a flow chart illustrating another method, implemented using the system shown in FIG. 1, and continuing from the flow chart shown in FIG. 2, for capturing data in a drone enabled environmental for testing soil and ecological decision making, according to an embodiment of the invention.

DETAILED DESCRIPTION

Figure 1:
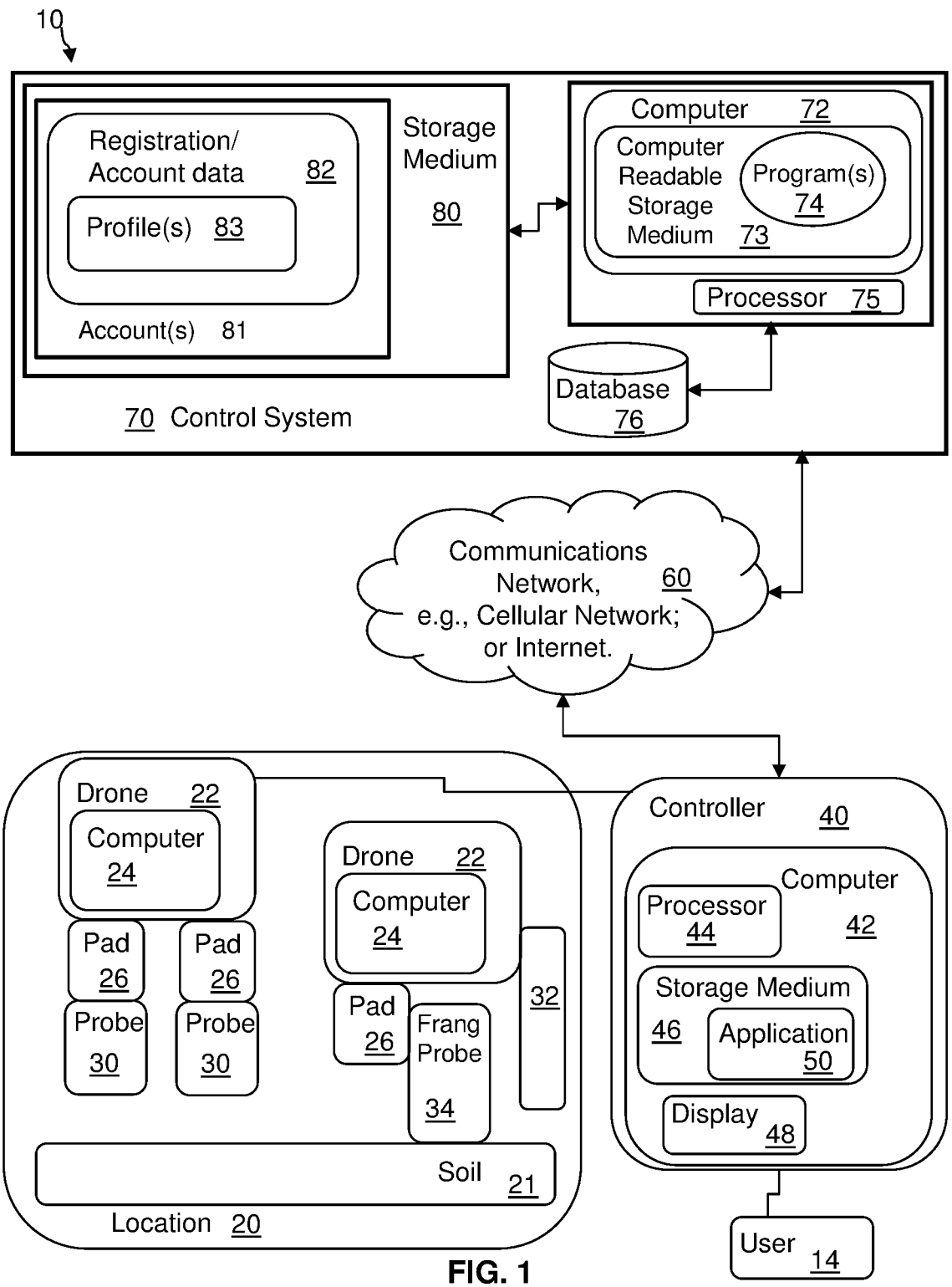
FIG. 1 is a schematic block diagram illustrating an overview of a system, system features or components, and methodology for capturing data in a drone enabled environmental for testing soil and ecological decision making, according to an embodiment of the present disclosure.

The following description with reference to the accompanying drawings is provided to assist in a comprehensive understanding of exemplary embodiments of the invention as defined by the claims and their equivalents. The description includes various specific details to assist in that understanding, but these are to be regarded as merely exemplary, and assist in providing clarity and conciseness. Accordingly, those of ordinary skill in the art will recognize that various changes and modifications of the embodiments described herein can be made without departing from the scope and spirit of the invention. In addition, descriptions of well-known functions and constructions may be omitted.

The terms and words used in the following description and claims are not limited to the bibliographical meanings, but, are merely used to enable a clear and consistent understanding of the invention. Accordingly, it should be apparent to those skilled in the art that the following description of exemplary embodiments of the present invention is provided for illustration purpose only and not for the purpose of limiting the invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces unless the context clearly dictates otherwise.

In general, it is understood that legal regulations can include legal regulations pertaining to property air space passed through or used in a drone flight path. In another example, a database can be populated, and updated and maintained, which can include legal regulation for reference. The database can be updated and expanded as needed over time, thus providing a database for legal regulation for reference when considering drone flights through respective air space and the regulation at respective locations. Such regulations, for example, in the United States, can include town, county, State and Federal regulations administered by the FAA (Federal Aviation Administration) of United States Department of Transportation. Also, fees and/or licenses may apply, and/or registration of drones and/or flight paths.

In one example, the possible flight paths, can require property owner permission for a flyover of the drone through airspace associated with a property.

The use of drones can be limited in many countries by airspace regulations, by property and privacy issues, and by safety concerns. For example, in the U.S.A., drone use is covered by Federal Air Regulation Part 107, which typically includes strict limits of altitude (typically not to exceed 400 feet above ground level), overflight restrictions, continual personal light-of-sight control and many other criteria. While drones are thus generally precluded by FAA regulation above 400 feet, flight below 400 feet over private property is generally precluded by property and privacy rights of the underlying landowner. Thus, unless one is flying above their own property, or in limited publicly-allowed airspace, individual permissions are required, in a complex patchwork of land use. Thus, embodiments of the present disclosure can use drones operating in an air space above a location or a farmer's plot which the drone user has permission to operate the drone, but below 400 feet above ground level. The drone operation can include measuring soil needs, and the moisture and air pollutant environment.

Electric aircraft, both piloted and autonomous, including small and larger aerial vehicles offer platforms for machine tasks such as package delivery, package pickup, remote sensing, agricultural seeding and support, photography, medical support, communications relay and many other uses. The use of drones can be limited in many countries by airspace regulations, by property and privacy issues, and by safety concerns. For example, in the U.S.A., drone use can be covered by Federal Air Regulations under the Federal Aviation Administration (FAA), which typically include limits of altitude (for example, not to exceed 400 feet above ground level), overflight restrictions, continual personal light-of-sight control and many other criteria.

However, while drones are generally precluded by FAA regulation above 400 feet, flight below 400 feet is allowed, however, such flight may be over private property and can be precluded by property and privacy rights of the landowner. Thus, unless a user is flying above their own property, or in publicly allowed airspace, individual permissions, that is, permission from landowners may be required, and thus can results in a complex patchwork of land use permission for a flight. In one example, regulations can include a requirement that a drone must be under direct line-of-sight control, or have other requirements, although, in some instances, waivers may be given in certain circumstances. Other requirement can include a drone having identifying serial numbers associating them with owners.

Embodiments and Examples

Figure 2:
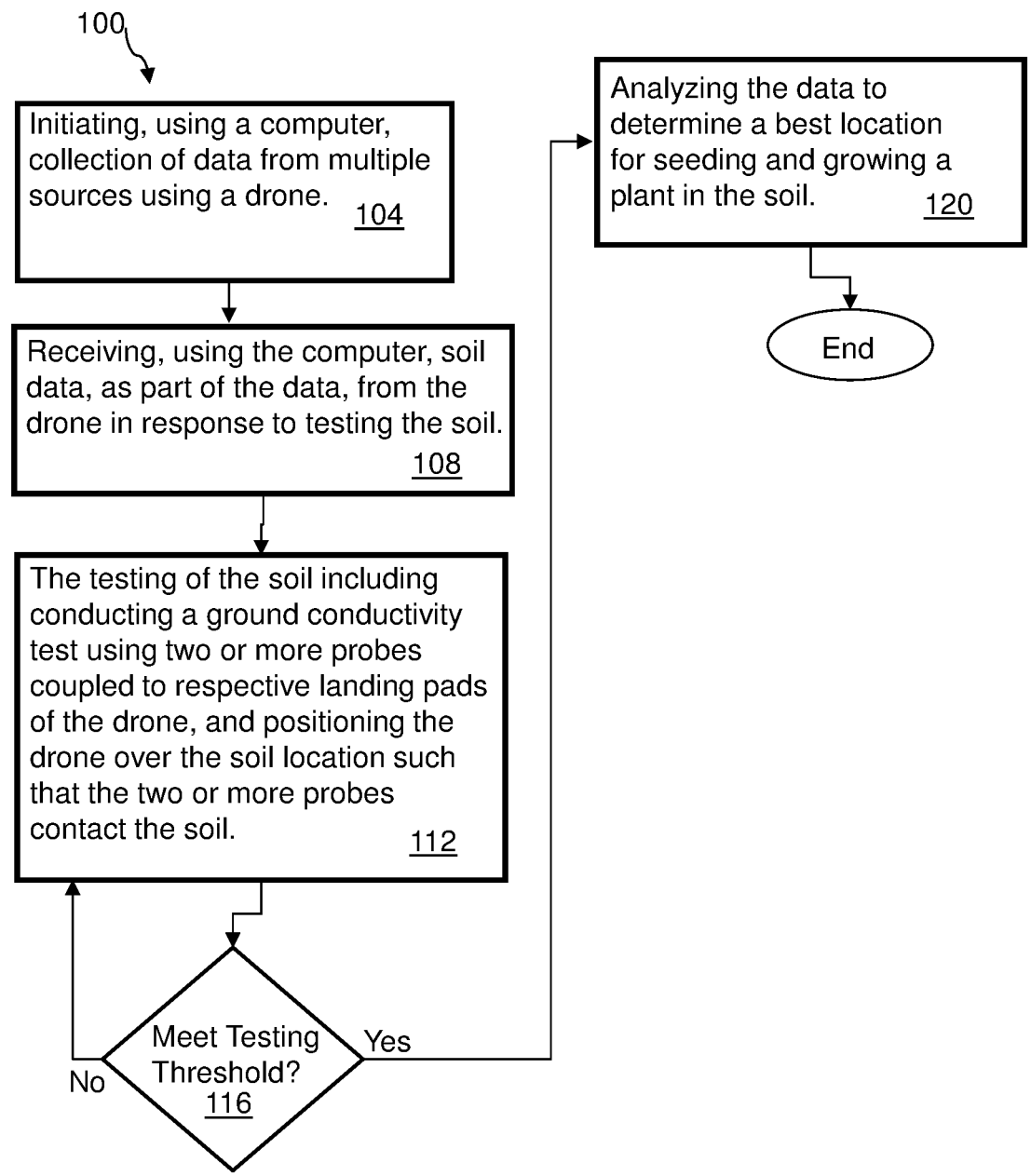
FIG. 2 is a flow chart illustrating a method, implemented using the system shown in FIG. 1, for capturing data in a drone enabled environmental for testing soil and ecological decision making, according to an embodiment of the present disclosure.

Referring to FIGS. 1 and 2, a computer-implemented method 100, using a system 10, for capturing data in a drone enabled environmental for testing soil and ecological decision making includes a series of operational blocks for implementing an embodiment according to the present disclosure. The method 100 includes initiating, using a computer, collection of data from multiple sources using a drone 22, as in block 104. The data is regarding information about soil 21 at a specified soil location 20, in response to the drone 22 flying over air space of a physical or geographical location 20 respective to the soil location 21 and/or landing at the soil location.

The drone 22 (shown in FIG. 1) can include a computer 24 or on-board computer. The drone includes landing pads or pads 26. In one example, four pads 26 can be attached to the drone. For convenience, the pads 26 shown in FIG. 1 are representative of more pads or a plurality of pads attached to the drone. In the embodiment shown in FIG. 1, the drone pads 26 include probes 30 extending outwardly from the pads. Also, the drone can communicate, using the computer 245 with a controller 40. The controller 40 includes a computer 42, processor 44, storage medium 46, an application 50 or application software, and a display 48. A user 14 can interact, that is, manipulate the controller 40 to operate one or more drones. The controller and alternatively, the drones 22 can communicate with a remote control system 70 via a communications network 60, for example a cellular network or the Internet. The control system 70 includes a storage medium 80, in which can be stored user accounts 81 having registration account data 82 including user profiles 83. The control system includes a computer 72, a computer readable storage medium 73 in which can be stored or embedded one or more programs 74, and the computer includes a processor 75 for executing the programs. The computer can also communicate with a database 76.

In another example, which will be discussed in more detail below, a drone can include a trialing conductive ribbon 32, or ribbon line electrode, as shown in FIG. 1.

The method 100 includes receiving, using the computer, soil data, as part of the data, from the drone in response to testing the soil, as in block 108. The testing of the soil can include conducting a ground conductivity test using two or more probes coupled to respective landing pads of the drone. In one example, the drone can have four probes, one attached to each landing pad. The drone can be positioned by flight over the soil location such that the two or more probes contact the soil, for example, hovering over the soil or landing on the soil location.

A testing threshold can be set for conducting a ground conductivity test, such as test results meeting minimum requirements. Such minimum requirements can include, for example, acceptable soil samples, acceptable soil contact, acceptable conductivity measurements. If the testing threshold is not met in block 116, the method returns to block 112, to initiate more tests. If the testing threshold is met, in block 116, the method continues to block 120 where the method 100 includes analyzing the data to determine a best location for seeding and growing a plant in the soil, as in block 120.

In one example, the ground conductivity test can use four probes coupled to four landing pads of the drone. The method can further include initiating electrical measurements using the four probes including a multiplicity of resistance measurements using a set of possible combinations of the four probes. The method includes receiving, using the computer, the electrical measurements from the drone as part of the soil data. The possible combinations of resistance measurements are shown in Table 2 and discussed below.

Operational blocks of the method 100 shown in FIG. 2, may be similar to operational blocks or used in the methods shown in FIGS. 3A and 3B. The methods shown in FIGS. 3A and 3B are intended as other example embodiments which can include aspects/operations shown and discussed previously in the present disclosure.

Referring to FIG. 3A, In another example according to the present disclosure, a method 200 can continue from block 108 of the method 100 shown in FIG. 2, and the method 200 can further include initiating, as part of the testing of the soil, physical contact of a probe into the soil, as in block 204. For example, the probe can be a plunge sensor, or a frangible probe 34 (shown in FIG. 1).

For a frangible probe 34, the probe can be frangible and break off the drone when physical resistance from the soil exceeds a stress threshold which can include a stress threshold which can include a tensile or a compressive threshold, as also in block 204. The method 200 includes receiving additional soil data, as part of the data, from the probe including stress data (or can be referred to as first stress data) related to the probe breaking off in response to the physical resistance from the soil exceeding the stress threshold, for example, a tensile or a compressive threshold, as in block 208. The method further includes analyzing the additional data to determine a best location for seeding and growing a plant in the soil, as in block 212.

In another embodiment according to the present disclosure, a method 250 continues from block 108 of the method 100 and can further include initiating, as part of the testing of the soil, physical contact of another probe on the soil, as in block 254, for example, a trail sensor. The another probe can be a ribbon-line electrode providing continual measurement data in response to being dragged along the soil.

The method 250 include analyzing the measurement data from the ribbon-line electrode to determine a best location for seeding and growing a plant in the soil, as in block 258.

The method 250 can further include in one example, receiving additional soil data, as part of the data, from the another probe (i.e., ribbon-line electrode) including stress data (which can be referred to as second stress data) related to the another probe breaking off in response to physical resistance from the soil exceeding a stress threshold, for example, a tensile or a compressive threshold. The method can include analyzing the additional soil data to determine a best location for seeding and growing a plant in the soil, in response to the receiving of the additional soil data.

In one example, the method 100 can further include initiating, as part of the testing of the soil, drilling into the soil, using a mini drill coupled to the drone. The method can further include, receiving soil samples from the drilling when the drone returns to a home base, generating soil sample data, as part of the data, from the soil samples, and analyzing the soil sample data to determine a best location for seeding and growing a plant in the soil.

In another example according to embodiments of the present disclosure, the method 100 can include the conducting of the ground conductivity test using four probes coupled to respective landing pads of the drone. The drone is positioned over the soil location such that the four probes contact the soil, and the method further includes initiating testing of the soil using resistance measurements between the four probes. The method includes receiving, using the computer, the soil data, as part of the data, including the resistance measurements from the drone in response to the testing the soil using the four probes. The data is analyzed to determine a best location for seeding and growing a plant in the soil.

In another example, the testing of the soil can use the resistance measurements between the four probes includes determining an optimum resistance using vector algebra.

In another example, the testing of the soil can use the resistance measurements between the four probes includes using a mathematical combination of the four probes.

Other Examples and Embodiments

Referring to FIG. 1, regarding creation and storage of user accounts, user accounts can refer to users of drones and also entities using drones for agricultural testing, for example, including soil samples. Account data, for instance, including profile data related to a user, and any data, personal or otherwise, can be collected and stored, for example, in the control system 70. It is understood that such data collection is done with the knowledge and consent of a user, and stored to preserve privacy, which is discussed in more detail below. Such data can include personal data, and data regarding personal items.

In one example, a user can register 82 with a drone service and have an account 81 with a user profile 83 on a control system 70, which is discussed in more detail below. For example, data can be collected using techniques as discussed above, for example, using cameras, and data can be uploaded to a user profile by the user.

In one example, a user can register an account which can include one or more profiles 83 as part of registration and/or account data 82. The registration can include profiles for each user having personalized data. For example, users can register using a website via their computer and GUI (Graphical User Interface) interface. The registration or account data 82 can include profiles 83 for an account 81 for each user. Such accounts can be stored on a control system 70, which can also include a database 76 for data storage.

Figure 4:
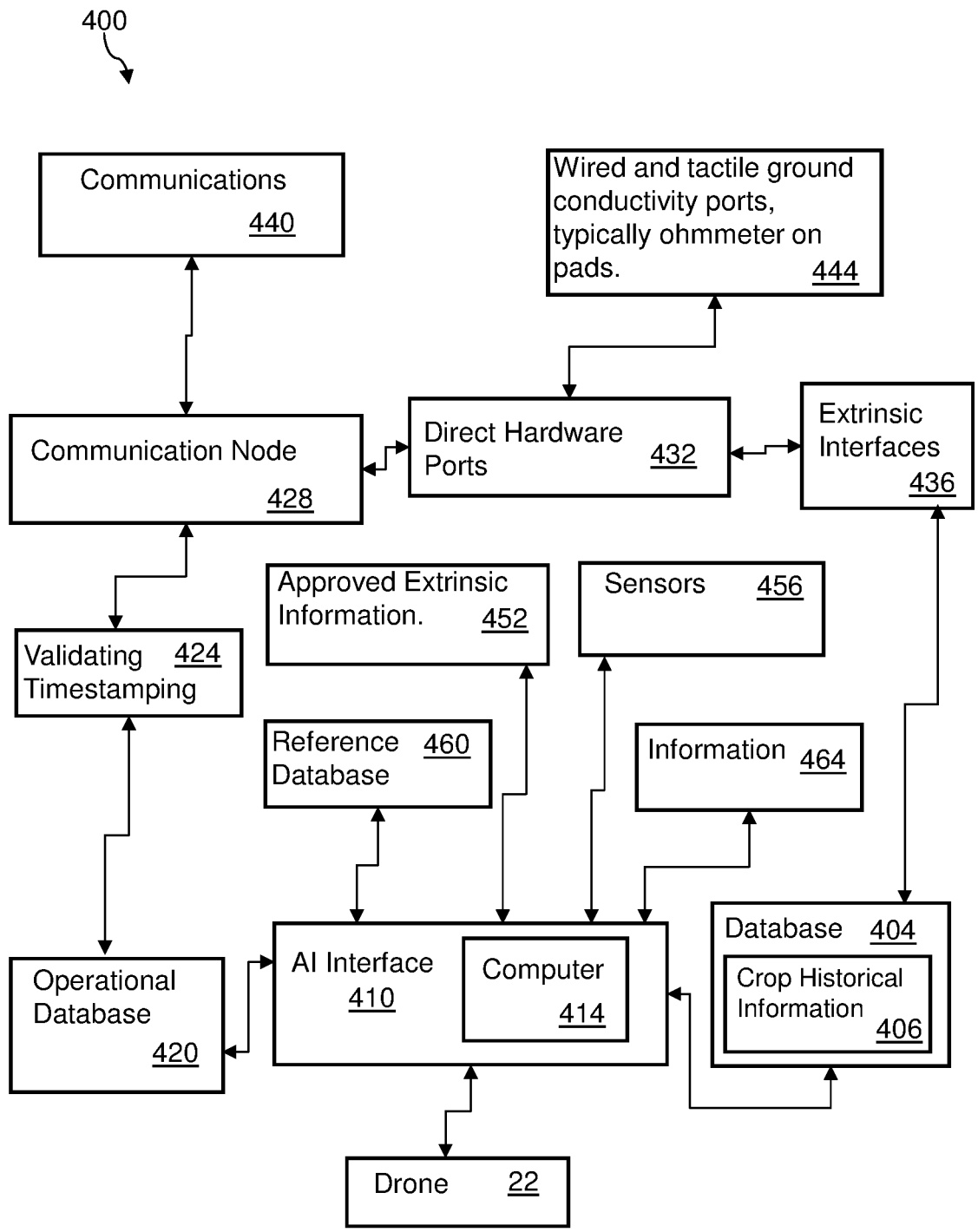
FIG. 4 is a functional schematic block diagram showing a series of operations and functional methodologies, for instructional purposes illustrating functional features of the present disclosure associated with the embodiments shown in the FIGS., for capturing data in a drone enabled environmental for testing soil and ecological decision making.

Additionally, methods and systems are discussed with reference to FIG. 4, which is a functional system 400 which includes components and operations for embodiments according to the present disclosure, and is used herein for reference when describing the methods and systems of the present disclosure. Additionally, the functional system 400, according to an embodiment of the present disclosure, depicts functional operation indicative of the embodiments discussed herein.

For example, as shown in FIG. 1, one or more items 24 are shown as representative of a plurality of items 24. One or more devices such as a controller 40 are shown as representative of a plurality of devices. The devices include a computer 42. A computer can be proximate to the location 20, remote from the location, or part of a mobile device, for example, a mobile device belonging to a user 14. The devices can control one or more drones 22. The computer 42 includes a processor 44 and a storage medium 46 which can include an application 50 embodying the method of the present disclosure. The computer 42 further includes the processor 44 for executing the application/software. The computer 42 can communicate with a communications network 60, e.g., the Internet. The drones 22 can also include computers 24 and can also communicate with the communications network 60, e.g., the Internet, directly or indirectly, or in combination with the computer 42 for controlling the drones and sending data for analysis. The application can embody the features of the method of the present disclosure as instructions.

An advantage of the methods and systems according to the present disclosure include enabling remote soil sample on a mobile platform, that is, using a drone, and for surface soil samples as well as deeper samples of soil stratification. The drone or drones can provide dynamic sensors, as opposed to static sensors which are placed in the ground at a singular location. That is, the dynamic sensors, using drones, can be placed over a large area by drones on a schedule, or on demand, or in a remote location.

In another example of advantages of embodiments of the present disclosure, the drone can include different toes of probes, such as trailing probes, or plunge type probes, and can also include frangible probes.

Further Embodiments and Examples

The methods and systems according to the present disclosure can include allowing the user to have multiple soil samples in a single trip from a drone base which can make the system be more agile and efficient. Soil stratification details can be communicated to the user/control system as the drill samples in a probe tube will keep the samples in order so that the user can have samples at every 2-4 cm from the ground.

The methods and systems according to the present disclosure provide a light weight, user friendly and, when trailing electrodes are use, the trailing electrodes can cover mores sample sites. The monitoring is not dependent of stationary devices that are installed in the ground. The present disclosure provides on-demand soil sampling and monitoring and can be without any human involvement. A user and/or system can gather soil samples from arbitrary and fairly distant points in a single trip as a result of the probes being attached to a drone.

In one example, a method and system can make use of various vectors to find an optimized solution. Vector algebra can be used to find optimum and complex resistances, sometimes using AI (Artificial Intelligence). In addition, multi-spectral imaging of light across various wavelengths can also be used. The present disclosure provides direct, or hands on methods were additionally to aerial imagery, data can be correlated with the help of the integrated ground sensors, frangible probes, flexible trailing components, soil sampling mechanisms, etc., in the drone or using the drone. The methods and systems according to the present disclosure can be on demand and able to get measurements without needing to install anything on or to the ground. Sensors can be low-weight and frangible, with minimal or no adverse agricultural or cultivational effect if unable to achieve and left in the ground. Embodiments of the present disclosure includes use of four probes coupled to four pads of the drone for performing ground conductivity tests. Additionally, embodiments of the present discuses can include use of frangible probes and ribbon-line electrodes (along with considerations of stress thresholds, such as, tensile or compressive thresholds) for performing drone-based tests.

Embodiments of the present disclosure include the use of drones for soil analysis (e.g., moisture analysis) using soil conductivity, resistance between two or more electrodes or probes contacting or inserted into the ground, and related approaches. In one example, four probes can be coupled to four pads of the drone for performing ground conductivity tests. Also, frangible probes and ribbon-line electrodes (along with considerations of tensile or compressive thresholds) can be used for performing drone-based tests, capturing data, and conducting measurements.

Embodiments of the present disclosure can include a correlation engine which leverages input from sensors such as: optical ground reflectivity from a drone's own internal camera; radio reflection from another drone's signal, or from another transmitter, to a drone; acoustic reflection from a drone to another drone, or from another acoustic source; or direct ground sampling of moisture from temporarily or embedded ground sources. Using the input data from sensors, the correlation engine can determine correlation of optimum ground moisture, add or reduce water as necessary. Additionally, agricultural solutions can be validated by observing past and currently growing, soil, and crop samples, both by itself and by extrinsic sensors.

In one example, a correlation engine can provide bands of optimized results, which are correlated with the actual situation of a field or agricultural plot in question. For example, first, the input to the drone is normalized by $1/H^2 \cos(\text{Theta})$; "H" can be a height over ground level (as seen by GPS (Global Positioning System)), and "Theta" can be an angle from vertical. Optimal results can be interpreted by the system and vary according to crop and soil. Optimal results can include such factors as in Table 1 below.

TABLE 1

| Sensor Type | More Moisture | Less Moisture |
|---|---|---|
| Multi-Spectral and Special Spectrum Optical | More reflectivity | Less reflectivity |
| Radio Frequency Reception | Higher signal strength | Lower signal strength |
| Acoustic Signature - still water | Less signature | More signature |
| Acoustic Signature - running water | More signature | Less signature |
| Direct ground conductivity and metering | Better conductivity, less ohmic resistance | Poorer Conductivity, higher ohmic resistance |

Additionally, the vast majority of modern drones have high-bandwidth two-way communications in the 2.4 or 5.8 GHz bands. In addition, the vast majority of modern drones have cameras which are—or can be "opened up" and/or tuned—for multi-spectrum, specific spectrum or infrared uses. This invention optionally calls for direct sampling by the drone, as well as interface with other drones. In the United States, drones are limited to a weight of 25 kg (55 lbs.). Drones, therefore, can land and make a measurement of ground conductivity with two or more probes attached to their landing pads. These probes can be connected to an ohmmeter. In addition, drones could optionally extract small surface samples for later use, for example, using a "dropped weight" approach. Also, drones could select a less populous area from the vegetation and with the methodology (moisture, pressure etc.), and a system and method can detect if the conditions are recommend for an area, and implement soil sampling using a soil sampling device integrated in the drone, and thereby "fetch" a soil sample such as a sliver sample for later testing. In one example, a physical probe could be frangible. If the frangible probe prevents the drone from take-off, the probe would break off at a pre-determined tension. In this situation, the probe breaking off would indicate soil density and hardness.

Embodiments of the present disclosure can integrate and assure not only the drone's mechanical systems, but the wide range of traditional radio frequency and thermal data sources and waveforms. Such radio frequency and thermal data sources can originate in the ground drone itself, in the ground and plots, in the air with its moisture and pollution, and in the growing species. Questions extrinsic to the drone can include detecting 'stated' humidity per the nearest ground sensor; detecting the predicted humidity; determining what is seen in the ground for 'as read' moisture, which can be compared to what the drone sensor(s) read.

Figure 6:
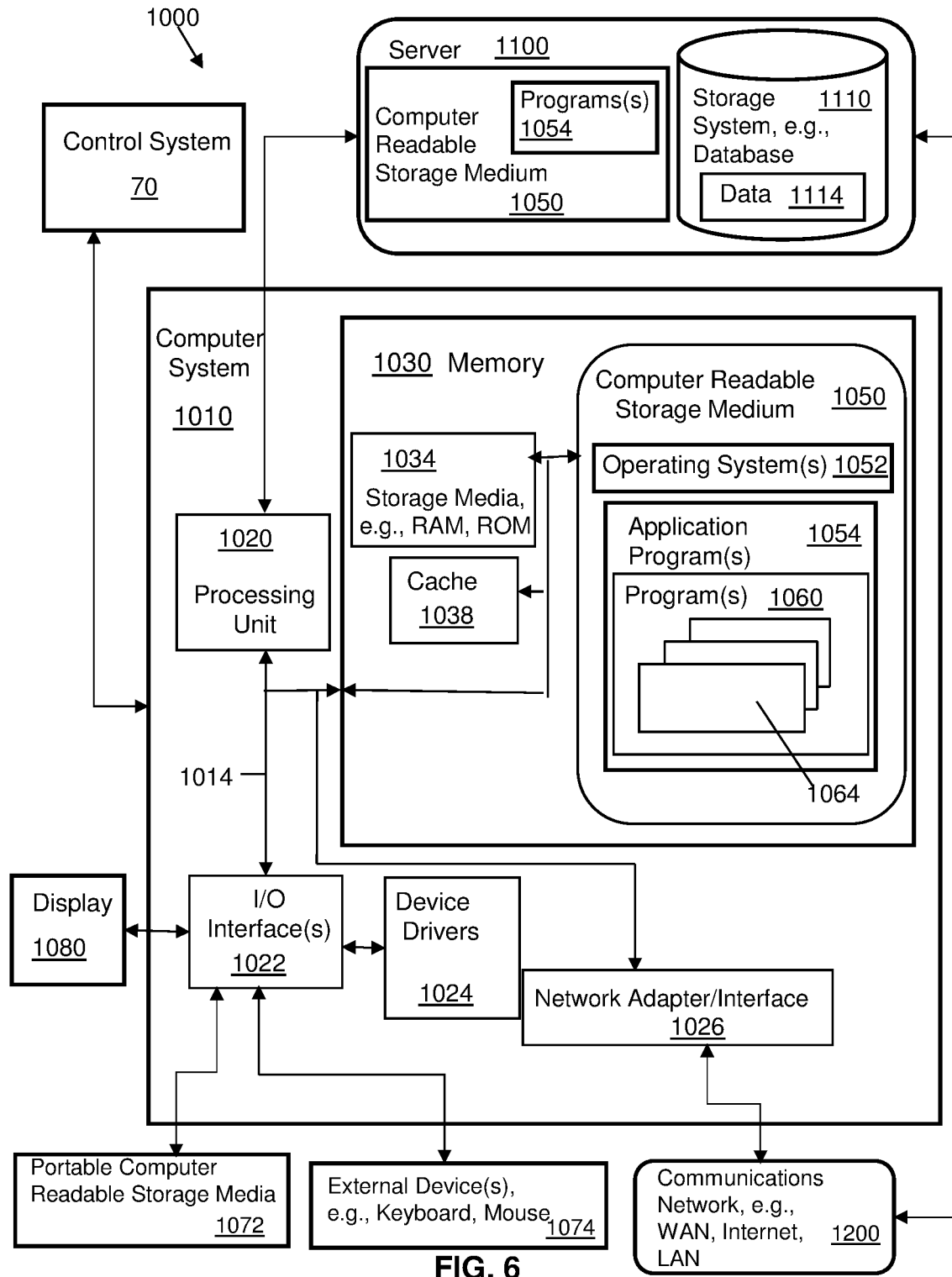
FIG. 6 is a schematic block diagram depicting a computer system according to an embodiment of the disclosure which may be incorporated, all or in part, in one or more computers or devices shown in FIG. 1, and cooperates with the systems and methods shown in the FIGS.

Referring to FIG. 6, in one embodiment or example, a system 400 or method can include a database and can include a blockchain ledger. Components of the system 400 communicate with each other and can communicate with the drone 22 using an AI interface. The system 400 can include a database 404 which can include crop historical information 406. An AI (Artificial Intelligence) interface 410 can include a computer 414, and can communicate with the drone 22. The system can include an operational database 420. The operational database can include continuing updates of reflectivity components. The operational database can implement validating timestamping 424. The system can include a communicating node 428 which can include a software-defined radio (SDR), and a cognitive waveform.

The communicating node 428 can receive communications 440 which can include radio frequency; near-field communications, GPS (Global Positioning System) data; two-way IoT (Internet of Things) and human communication. The system includes direct hardware ports 432. The direct hardware ports 432 can receive wired, or tactile ground conductivity ports, or ohmmeters on pads as represented in block 444. The system can also include extrinsic interfaces 436. Approved extrinsic information 452 can include control of irrigation equipment, valves, etc. A reference database 460 can include a run-time odometer, temperature and moisture records. Sensors 456 on the drone 22 can include sensors for air pressure, outside temperature, outside environment, direction, video, or inside flows and/or pressure. Other information 464 can include high moisture, operational, low priority, or informational.

Typically, the drone can include a camera which can detect soil moisture content by direction observation, and AI (Artificial Intelligence) instantiation. The drone can also permit sophisticated measurement of ohmic resistance and impedance using inexpensive, break-away sensors on its pads. Typical inexpensive consumer drones have four landing pads. These sensors can have both "plunge" (input in soil) and "trail" capability. The plunge sensors use the weight of the drone to imbed solid electrodes, and they are broken off in the event of too rigid soil on extraction. This soil condition itself can indicate agricultural sufficiency or insufficiency based on the breaking-off of the electrode. The trail sensors have flowing and following ribbon-line electrodes for continual measurement. Sophisticated analysis may be done using both direct and quasi-sheet resistance measurement.

Figure 5:
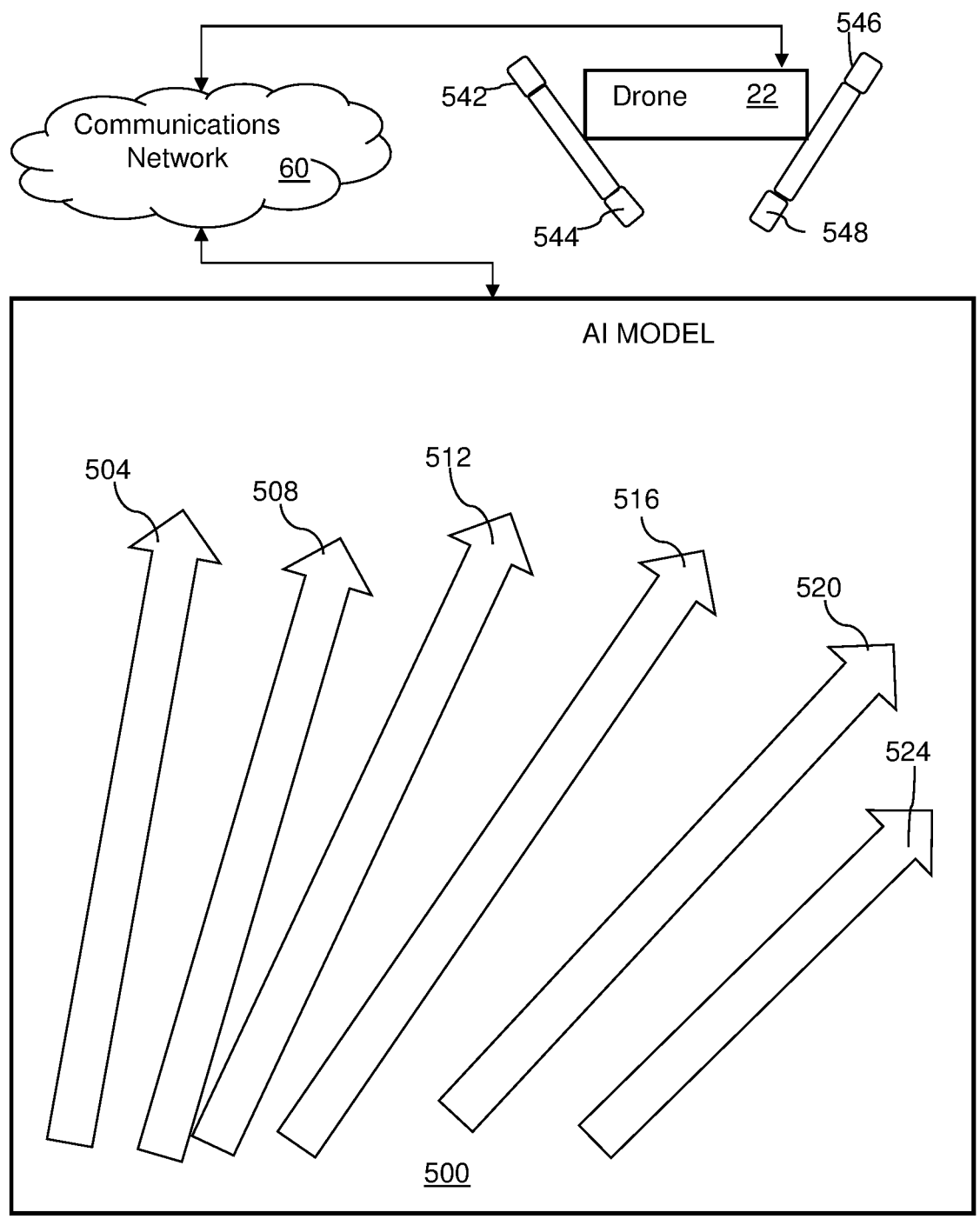
FIG. 5 is a schematic block diagram illustrating a system depicting another aspect of the present disclosure including vector analysis of resistance.

Referring to FIG. 5, readings from various vectors can be incorporated in an AI (Artificial Intelligence) model 500. The various vectors can use least-square positioning and interpolation for optimized results. Vector 504 includes resistance and impedance from a drone. Such measurements can have 21 or more possibilities with 4 or more probes. Vector 508 can include least squares matrix solutions which can be reiterated. Vector 512 can include humidity input from local weather forecasts. Vector 516 can include humidity indications from direct measurements. Vector 520 can include moisture input from potential embedded ground sensors. Vector 524 can include optical input from a drone.

In one example, there are many Radio-Frequency waveforms impacting the drone (Wi-Fi, GPS, etc.). Other radio signals may emanate from the drone (for example, from a camera, position, resistance, etc.). In general, atmospheric moisture impedes UHF (Ultra High Frequency) signals selectively. Typically, the more moisture, the lower the signal, with this effect being more pronounced, the higher the frequency. Pollution-based particulate can also impede transmission, particularly at EHF (Extremely High Frequency) frequencies. The AI component can measure these factors, and when they count most, for example, below 400 feet from ground level.

For example, a drone with four pads can have 21 DC (Direct Current) resistance, quasi sheet-resistance, AC (Alternating Current) impedance and pulse combinations possible. For example, combinations are shown in Table 2 below.

TABLE 2

| | | | | |
|---|---|---|---|---|
| Sensor 542 to Sensor 546 | Sensor 546 to sensor 548 | Sensor 548 to Sensor 544 | Sensor 544 to Sensors 542, 546 | Sensors 542, 546 to Sensors 544, 548 |
| Sensor 542 to Sensor 548 | Sensor 546 to Sensor 544 | Sensor 548 to Sensors 542, 546 | Sensor 544 to Sensors 546, 548 | Sensor 542, 548 to Sensors 546, 544 |
| Sensor 542 to Sensor 544 | Sensor 546 to Sensors 542, 544 | Sensor 548 to Sensors 542, 544 | Sensor 544 to Sensors 542, 546 | Sensors 542, 544 to Sensors 546, 548 |
| Sensor 542 to Sensors 546, 548 | Sensor 546 to Sensors 546, 548 | Sensor 548 to Sensors 542, 546, 544 | | |
| Sensor 542 to Sensors 548, 546 | Sensor 546 to Sensors 542, 544, 548 | | | |
| Sensor 542 to Sensors 546, 548, 544 | | | | |

Embodiments of the present disclosure can provide transactional opportunities for AI for best-path analysis of overfly routes and corridor construction. Further, embodiments of the present disclosure can include radio and/or acoustic reflection or soil sampling. In one example, precision soil sampling can take a sample every half acre, providing two samples per acre. These locations can be marked using existing GPS technology, which are used to develop detailed application maps. The maps can allow the farmer to apply inputs at a very high level of precision and accuracy. A sampling system can be attached to the drone and take samples from a remote spot.

More Examples and Embodiments

In the embodiment of the present disclosure shown in FIGS. 1 and 2, a computer can be part of a remote computer or a remote server, for example, remote server 1100 (FIG. 6). In another example, the computer 72 can be part of a control system 70 and provide execution of the functions of the present disclosure. In another embodiment, a computer can be part of a mobile device and provide execution of the functions of the present disclosure. In still another embodiment, parts of the execution of functions of the present disclosure can be shared between the control system computer and the mobile device computer, for example, the control system function as a back end of a program or programs embodying the present disclosure and the mobile device computer functioning as a front end of the program or programs.

The computer can be part of the mobile device or a controller, or a remote computer communicating with the mobile device or controller. In another example, a mobile device and a remote computer can work in combination to implement the method of the present disclosure using stored program code or instructions to execute the features of the method(s) described herein. In one example, the mobile device can include a computer 42 having a processor 44 and a storage medium 46 which stores an application 50. The application can incorporate program instructions for executing the features of the present disclosure using the processor 44. In another example, the mobile device application or computer software can have program instructions executable for a front end of a software application incorporating the features of the method of the present disclosure in program instructions, while a back end program or programs 74, of the software application, stored on the computer 72 of the control system 70 communicates with the mobile device computer and executes other features of the method. The control system 70 and the mobile device or computer 42 can communicate using a communications network 60, for example, the Internet.

Thereby, the method 100 according to an embodiment of the present disclosure, can be incorporated in one or more computer programs or an application 40 stored on an electronic storage medium 34, and executable by the processor 32, as part of the computer on the mobile device. For example, a mobile device can communicate with the control system 70, and in another example, a device such as a video feed device can communicate directly with the control system 70. Other users (not shown) may have similar mobile devices which communicate with the control system similarly. The application can be stored, all or in part, on a computer or a computer in a mobile device and at a control system communicating with the mobile device, for example, using the communications network 50, such as the Internet. It is envisioned that the application can access all or part of program instructions to implement the method of the present disclosure. The program or application can communicate with a remote computer system via a communications network 50 (e.g., the Internet) and access data, and cooperate with program(s) stored on the remote computer system. Such interactions and mechanisms are described in further detail herein and referred to regarding components of a computer system, such as computer readable storage media, which are shown in one embodiment in FIG. 6 and described in more detail in regards thereto referring to one or more computer systems 1010.

Thus, in one example, a control system 70 is in communication with the computer 42, and the computer can include the application or software 50. The computer 42, or a computer in a mobile device (not shown) communicates with the control system 70 using the communications network 60.

In another example, the control system 70 can have a front-end computer belonging to one or more users, and a back-end computer embodied as the control system.

Also, referring to FIG. 1, a device can include a computer 42, computer readable storage medium 46, and operating systems, and/or programs, and/or a software application 50, which can include program instructions executable using a processor 44. These features are shown herein in FIG. 1, and also in an embodiment of a computer system shown in FIG. 6 referring to one or more computer systems 1010, which may include one or more generic computer components.

The method according to the present disclosure, can include a computer for implementing the features of the method, according to the present disclosure, as part of a control system. In another example, a computer as part of a control system can work in corporation with a mobile device computer in concert with communication system for implementing the features of the method according to the present disclosure. In another example, a computer for implementing the features of the method can be part of a mobile device and thus implement the method locally.

Specifically, regarding the control system 70, the device(s) 25, in one example the devices which can belong to one or more users, and can be in communication with the control system 70 via the communications network 60. In the embodiment of the control system shown in FIG. 1, the control system 70 includes a computer 72 having a database 76 and one or more programs 74 stored on a computer readable storage medium 73. In the embodiment of the disclosure shown in FIG. 1, the devices 25 communicate with the control system 70 and the one or more programs 74 stored on a computer readable storage medium 73. The control system includes the computer 72 having a processor 75, which also has access to the database 76.

The control system 70 can include a storage medium 80 for maintaining a registration 82 of users and their devices for analysis of the audio input. Such registration can include user profiles 83, which can include user data supplied by the users in reference to registering and setting-up an account. In an embodiment, the method and system which incorporates the present disclosure includes the control system (generally referred to as the back-end) in combination and cooperation with a front end of the method and system, which can be the application 40. In one example, the application 50 is stored on a device, for example, a computer on location 42, and can access data and additional programs at a back end of the application, e.g., control system 70.

The control system can also be part of a software application implementation, and/or represent a software application having a front-end user part and a back-end part providing functionality. In an embodiment, the method and system which incorporates the present disclosure includes the control system (which can be generally referred to as the back-end of the software application which incorporates a part of the method and system of an embodiment of the present application) in combination and cooperation with a front end of the software application incorporating another part of the method and system of the present application at the device, as in the example shown in FIG. 1 of a device and computer 42 having the application 50. The application 50 is stored on the computer 42 and can access data and additional programs at the back end of the application, for example, in the program(s) 74 stored in the control system 70.

The program(s) 74 can include, all or in part, a series of executable steps for implementing the method of the present disclosure. A program, incorporating the present method, can be all or in part stored in the computer readable storage medium on the control system or, in all or in part, on a computer 42 or device. It is envisioned that the control system 70 can not only store the profile of users, but in one embodiment, can interact with a website for viewing on a display of a device such as a mobile device, or in another example the Internet, and receive user input related to the method and system of the present disclosure. It is understood that FIG. 1 depicts one or more profiles 83, however, the method can include multiple profiles, users, registrations, etc. It is envisioned that a plurality of users or a group of users can register and provide profiles using the control system for use according to the method and system of the present disclosure.

Still Further Embodiments and Examples

It is understood that the features shown in some of the FIGS., for example block diagrams, are functional representations of features of the present disclosure. Such features are shown in embodiments of the systems and methods of the present disclosure for illustrative purposes to clarify the functionality of features of the present disclosure.

The methods and systems of the present disclosure can include a series of operation blocks for implementing one or more embodiments according to the present disclosure. In some examples, operational blocks of one or more FIGS. may be similar to operational blocks another FIG. A method shown in one FIG. may be another example embodiment which can include aspects/operations shown in another FIG. and discussed previously.

Additional Embodiments and Examples

Regarding collection of data with respect to the present disclosure, such uploading or generation of profiles is voluntary by the one or more users, and thus initiated by and with the approval of a user. Thereby, a user can opt-in to establishing an account having a profile according to the present disclosure. Similarly, data received by the system or inputted or received as an input is voluntary by one or more users, and thus initiated by and with the approval of the user. Thereby, a user can opt-in to input data according to the present disclosure. Such user approval also includes a user's option to cancel such profile or account, and/or input of data, and thus opt-out, at the user's discretion, of capturing communications and data. Further, any data stored or collected is understood to be intended to be securely stored and unavailable without authorization by the user, and not available to the public and/or unauthorized users. Such stored data is understood to be deleted at the request of the user and deleted in a secure manner. Also, any use of such stored data is understood to be, according to the present disclosure, only with the user's authorization and consent.

In one or more embodiments of the present invention, a user(s) can opt-in or register with a control system, voluntarily providing data and/or information in the process, with the user's consent and authorization, where the data is stored and used in the one or more methods of the present disclosure. Also, a user(s) can register one or more user electronic devices for use with the one or more methods and systems according to the present disclosure. As part of a registration, a user can also identify and authorize access to one or more activities or other systems (e.g., audio and/or video systems). Such opt-in of registration and authorizing collection and/or storage of data is voluntary and a user may request deletion of data (including a profile and/or profile data), un-registering, and/or opt-out of any registration. It is understood that such opting-out includes disposal of all data in a secure manner. A user interface can also allow a user or an individual to remove all their historical data.

Other Additional Embodiments and Examples

In one example, Artificial Intelligence (AI) can be used, all or in part, for a learning model for analyzing data associated with items and assets.

In another example, the control system 70 can be all or part of an Artificial Intelligence (AI) system. For example, the control system can be one or more components of an AI system.

It is also understood that the method 100 according to an embodiment of the present disclosure, can be incorporated into (Artificial Intelligence) AI devices, which can communicate with respective AI systems, and respective AI system platforms. Thereby, such programs or an application incorporating the method of the present disclosure, as discussed above, can be part of an AI system. In one embodiment according to the present invention, it is envisioned that the control system can communicate with an AI system, or in another example can be part of an AI system. The control system can also represent a software application having a front-end user part and a back-end part providing functionality, which can in one or more examples, interact with, encompass, or be part of larger systems, such as an AI system. In one example, an AI device can be associated with an AI system, which can be all or in part, a control system and/or a content delivery system, and be remote from an AI device. Such an AI system can be represented by one or more servers storing programs on computer readable medium which can communicate with one or more AI devices. The AI system can communicate with the control system, and in one or more embodiments, the control system can be all or part of the AI system or vice versa.

It is understood that as discussed herein, a download or downloadable data can be initiated using a voice command or using a mouse, touch screen, etc. In such examples a mobile device can be user initiated, or an AI device can be used with consent and permission of users. Other examples of AI devices include devices which include a microphone, speaker, and can access a cellular network or mobile network, a communications network, or the Internet, for example, a vehicle having a computer and having cellular or satellite communications, or in another example, IoT (Internet of Things) devices, such as appliances, having cellular network or Internet access.

Further Discussion Regarding Examples and Embodiments

It is understood that a set or group is a collection of distinct objects or elements. The objects or elements that make up a set or group can be anything, for example, numbers, letters of the alphabet, other sets, a number of people or users, and so on. It is further understood that a set or group can be one element, for example, one thing or a number, in other words, a set of one element, for example, one or more users or people or participants.

The descriptions of the various embodiments of the present invention have been presented for purposes of illustration, but are not intended to be exhaustive or limited to the embodiments disclosed. Likewise, examples of features or functionality of the embodiments of the disclosure described herein, whether used in the description of a particular embodiment, or listed as examples, are not intended to limit the embodiments of the disclosure described herein, or limit the disclosure to the examples described herein. Such examples are intended to be examples or exemplary, and non-exhaustive. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further Examples and Aspects

Referring to FIG. 6, an embodiment of system or computer environment 1000, according to the present disclosure, includes a computer system 1010 shown in the form of a generic computing device. The method 100, for example, may be embodied in a program 1060, including program instructions, embodied on a computer readable storage device, or a computer readable storage medium, for example, generally referred to as computer memory 1030 and more specifically, computer readable storage medium 1050. Such memory and/or computer readable storage media includes non-volatile memory or non-volatile storage, also known and referred to non-transient computer readable storage media, or non-transitory computer readable storage media. For example, such non-volatile memory can also be disk storage devices, including one or more hard drives. For example, memory 1030 can include storage media 1034 such as RAM (Random Access Memory) or ROM (Read Only Memory), and cache memory 1038. The program 1060 is executable by the processor 1020 of the computer system 1010 (to execute program steps, code, or program code). Additional data storage may also be embodied as a database 1110 which includes data 1114. The computer system 1010 and the program 1060 are generic representations of a computer and program that may be local to a user, or provided as a remote service (for example, as a cloud based service), and may be provided in further examples, using a website accessible using the communications network 1200 (e.g., interacting with a network, the Internet, or cloud services). It is understood that the computer system 1010 also generically represents herein a computer device or a computer included in a device, such as a laptop or desktop computer, etc., or one or more servers, alone or as part of a datacenter. The computer system can include a network adapter/interface 1026, and an input/output (I/O) interface(s) 1022. The I/O interface 1022 allows for input and output of data with an external device 1074 that may be connected to the computer system. The network adapter/interface 1026 may provide communications between the computer system a network generically shown as the communications network 1200.

The computer 1010 may be described in the general context of computer system-executable instructions, such as program modules, being executed by a computer system. Generally, program modules may include routines, programs, objects, components, logic, data structures, and so on that perform particular tasks or implement particular abstract data types. The method steps and system components and techniques may be embodied in modules of the program 1060 for performing the tasks of each of the steps of the method and system. The modules are generically represented in the figure as program modules 1064. The program 1060 and program modules 1064 can execute specific steps, routines, sub-routines, instructions or code, of the program.

The method of the present disclosure can be run locally on a device such as a mobile device, or can be run a service, for instance, on the server 1100 which may be remote and can be accessed using the communications network 1200. The program or executable instructions may also be offered as a service by a provider. The computer 1010 may be practiced in a distributed cloud computing environment where tasks are performed by remote processing devices that are linked through a communications network 1200. In a distributed cloud computing environment, program modules may be located in both local and remote computer system storage media including memory storage devices.

More specifically, the system or computer environment 1000 includes the computer system 1010 shown in the form of a general-purpose computing device with illustrative periphery devices. The components of the computer system 1010 may include, but are not limited to, one or more processors or processing units 1020, a system memory 1030, and a bus 1014 that couples various system components including system memory 1030 to processor 1020.

The bus 1014 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer 1010 can include a variety of computer readable media. Such media may be any available media that is accessible by the computer 1010 (e.g., computer system, or server), and can include both volatile and non-volatile media, as well as, removable and non-removable media. Computer memory 1030 can include additional computer readable media in the form of volatile memory, such as random access memory (RAM) 1034, and/or cache memory 1038. The computer 1010 may further include other removable/non-removable, volatile/non-volatile computer storage media, in one example, portable computer readable storage media 1072. In one embodiment, the computer readable storage medium 1050 can be provided for reading from and writing to a non-removable, non-volatile magnetic media. The computer readable storage medium 1050 can be embodied, for example, as a hard drive. Additional memory and data storage can be provided, for example, as the storage system 1110 (e.g., a database) for storing data 1114 and communicating with the processing unit 1020. The database can be stored on or be part of a server 1100. Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 1014 by one or more data media interfaces. As will be further depicted and described below, memory 1030 may include at least one program product which can include one or more program modules that are configured to carry out the functions of embodiments of the present invention.

The method(s) described in the present disclosure, for example, may be embodied in one or more computer programs, generically referred to as a program 1060 and can be stored in memory 1030 in the computer readable storage medium 1050. The program 1060 can include program modules 1064. The program modules 1064 can generally carry out functions and/or methodologies of embodiments of the invention as described herein. The one or more programs 1060 are stored in memory 1030 and are executable by the processing unit 1020. By way of example, the memory 1030 may store an operating system 1052, one or more application programs 1054, other program modules, and program data on the computer readable storage medium 1050. It is understood that the program 1060, and the operating system 1052 and the application program(s) 1054 stored on the computer readable storage medium 1050 are similarly executable by the processing unit 1020. It is also understood that the application 1054 and program(s) 1060 are shown generically, and can include all of, or be part of, one or more applications and program discussed in the present disclosure, or vice versa, that is, the application 1054 and program 1060 can be all or part of one or more applications or programs which are discussed in the present disclosure. It is also understood that a control system 70, communicating with a computer system, can include all or part of the computer system 1010 and its components, and/or the control system can communicate with all or part of the computer system 1010 and its components as a remote computer system, to achieve the control system functions described in the present disclosure. The control system function, for example, can include storing, processing, and executing software instructions to perform the functions of the present disclosure. It is also understood that the one or more computers or computer systems shown in FIG. 1 similarly can include all or part of the computer system 1010 and its components, and/or the one or more computers can communicate with all or part of the computer system 1010 and its components as a remote computer system, to achieve the computer functions described in the present disclosure.

In an embodiment according to the present disclosure, one or more programs can be stored in one or more computer readable storage media such that a program is embodied and/or encoded in a computer readable storage medium. In one example, the stored program can include program instructions for execution by a processor, or a computer system having a processor, to perform a method or cause the computer system to perform one or more functions. For example, in one embedment according to the present disclosure, a program embodying a method is embodied in, or encoded in, a computer readable storage medium, which includes and is defined as, a non-transient or non-transitory computer readable storage medium. Thus, embodiments or examples according to the present disclosure, of a computer readable storage medium do not include a signal, and embodiments can include one or more non-transient or non-transitory computer readable storage mediums. Thereby, in one example, a program can be recorded on a computer readable storage medium and become structurally and functionally interrelated to the medium.

The computer 1010 may also communicate with one or more external devices 1074 such as a keyboard, a pointing device, a display 1080, etc.; one or more devices that enable a user to interact with the computer 1010; and/or any devices (e.g., network card, modem, etc.) that enables the computer 1010 to communicate with one or more other computing devices. Such communication can occur via the Input/Output (I/O) interfaces 1022. Still yet, the computer 1010 can communicate with one or more networks 1200 such as a local area network (LAN), a general wide area network (WAN), and/or a public network (e.g., the Internet) via network adapter/interface 1026. As depicted, network adapter 1026 communicates with the other components of the computer 1010 via bus 1014. It should be understood that although not shown, other hardware and/or software components could be used in conjunction with the computer 1010. Examples, include, but are not limited to: microcode, device drivers 1024, redundant processing units, external disk drive arrays, RAID systems, tape drives, and data archival storage systems, etc.

It is understood that a computer or a program running on the computer 1010 may communicate with a server, embodied as the server 1100, via one or more communications networks, embodied as the communications network 1200. The communications network 1200 may include transmission media and network links which include, for example, wireless, wired, or optical fiber, and routers, firewalls, switches, and gateway computers. The communications network may include connections, such as wire, wireless communication links, or fiber optic cables. A communications network may represent a worldwide collection of networks and gateways, such as the Internet, that use various protocols to communicate with one another, such as Lightweight Directory Access Protocol (LDAP), Transport Control Protocol/Internet Protocol (TCP/IP), Hypertext Transport Protocol (HTTP), Wireless Application Protocol (WAP), etc. A network may also include a number of different types of networks, such as, for example, an intranet, a local area network (LAN), or a wide area network (WAN).

In one example, a computer can use a network which may access a website on the Web (World Wide Web) using the Internet. In one embodiment, a computer 1010, including a mobile device, can use a communications system or network 1200 which can include the Internet, or a public switched telephone network (PSTN) for example, a cellular network. The PSTN may include telephone lines, fiber optic cables, microwave transmission links, cellular networks, and communications satellites. The Internet may facilitate numerous searching and texting techniques, for example, using a cell phone or laptop computer to send queries to search engines via text messages (SMS), Multimedia Messaging Service (MMS) (related to SMS), email, or a web browser. The search engine can retrieve search results, that is, links to websites, documents, or other downloadable data that correspond to the query, and similarly, provide the search results to the user via the device as, for example, a web page of search results.

More Examples and Aspects

Figure 7:
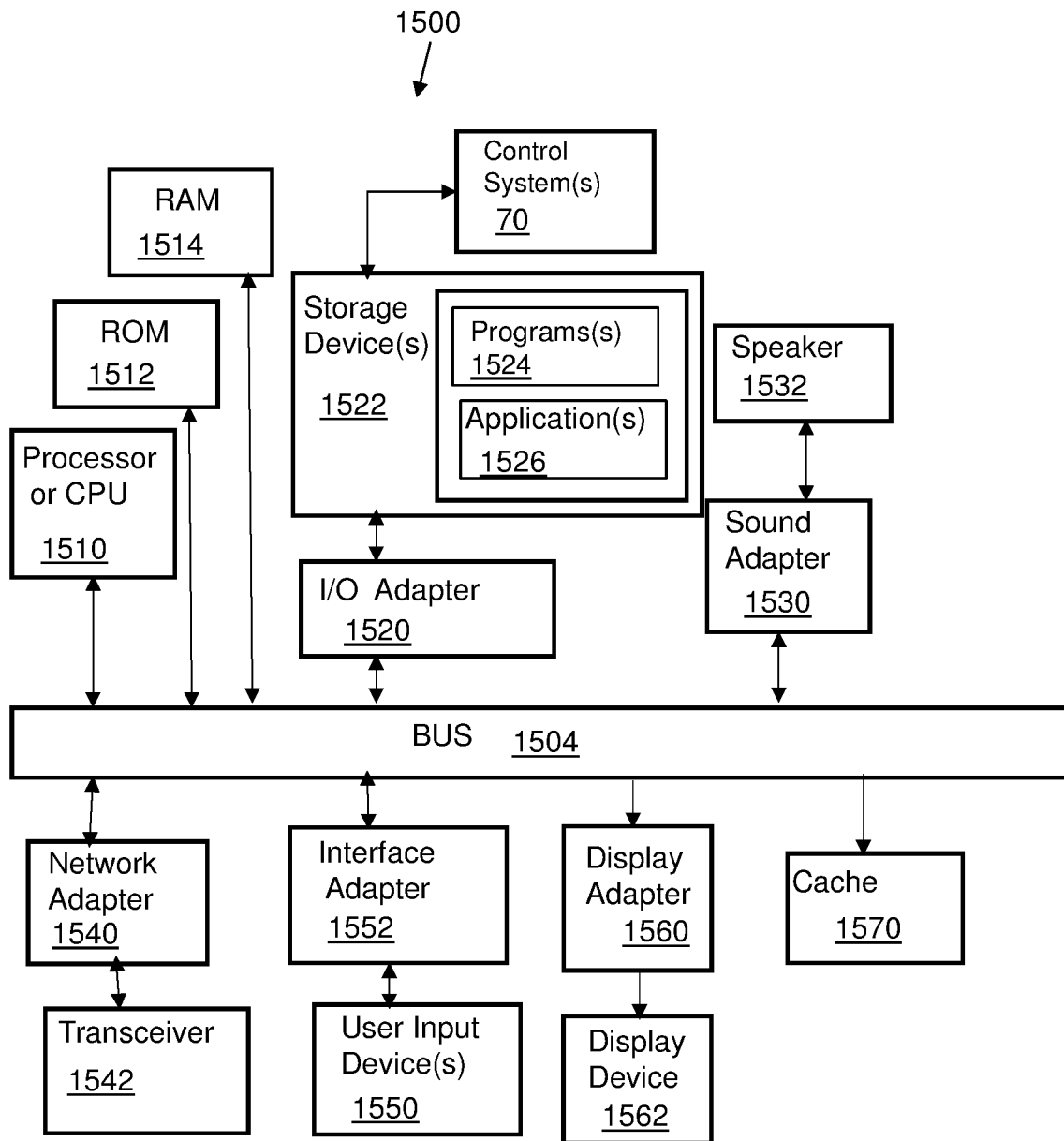
FIG. 7 is a schematic block diagram of a system depicting system components interconnected using a bus. The components for use, in all or in part, with the embodiments of the present disclosure, in accordance with one or more embodiments of the present disclosure.

Referring to FIG. 7, an example system 1500 for use with the embodiments of the present disclosure is depicted. The system 1500 includes a plurality of components and elements connected via a system bus 1504 (also referred to as a bus). At least one processor (CPU) 1510, is connected to other components via the system bus 1504. A cache 1570, a Read Only Memory (ROM) 1512, a Random Access Memory (RAM) 1514, an input/output (I/O) adapter 1520, a sound adapter 1530, a network adapter 1540, a user interface adapter 1552, a display adapter 1560 and a display device 1562, are also operatively coupled to the system bus 1504 of the system 1500.

One or more storage devices 1522 are operatively coupled to the system bus 1504 by the I/O adapter 1520. The storage device 1522, for example, can be any of a disk storage device (e.g., a magnetic or optical disk storage device), a solid state magnetic device, and so forth. The storage device 1522 can be the same type of storage device or different types of storage devices. The storage device can include, for example, but not limited to, a hard drive or flash memory and be used to store one or more programs 1524 or applications 1526. The programs and applications are shown as generic components and are executable using the processor 1510. The program 1524 and/or application 1526 can include all of, or part of, programs or applications discussed in the present disclosure, as well vice versa, that is, the program 1524 and the application 1526 can be part of other applications or program discussed in the present disclosure. The storage device can communicate with the control system 70 which has various functions as described in the present disclosure.

A speaker 1532 is operatively coupled to system bus 1504 by the sound adapter 1530. A transceiver 1542 is operatively coupled to system bus 1504 by the network adapter 1540. A display 1562 is operatively coupled to the system bus 1504 by the display adapter 1560.

One or more user input devices 1550 are operatively coupled to the system bus 1504 by the user interface adapter 1552. The user input devices 1550 can be, for example, any of a keyboard, a mouse, a keypad, an image capture device, a motion sensing device, a microphone, a device incorporating the functionality of at least two of the preceding devices, and so forth. Other types of input devices can also be used, while maintaining the spirit of the present invention. The user input devices 1550 can be the same type of user input device or different types of user input devices. The user input devices 1550 are used to input and output information to and from the system 1500.

Other Aspects and Examples

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures of the present disclosure illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Further Additional Aspects and Examples

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
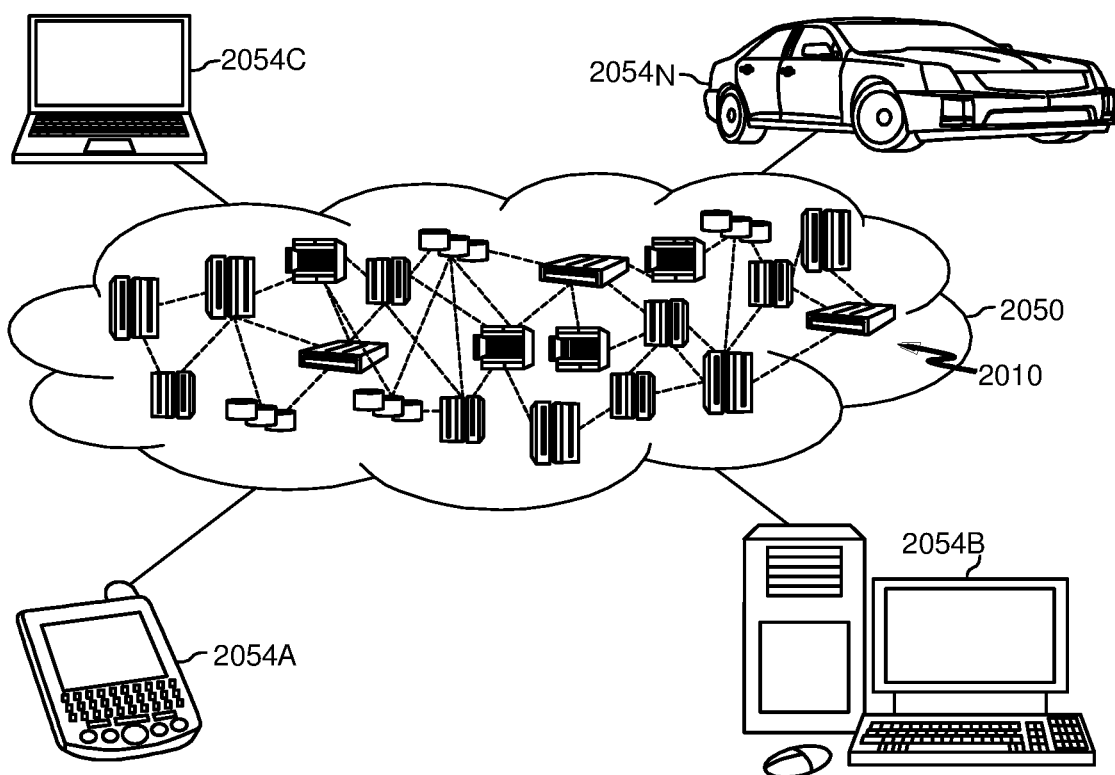
FIG. 8 is a block diagram depicting a cloud computing environment according to an embodiment of the present invention.

Referring now to FIG. 8, illustrative cloud computing environment 2050 is depicted. As shown, cloud computing environment 2050 includes one or more cloud computing nodes 2010 with which local computing devices used by cloud consumers, such as, for example, personal digital assistant (PDA) or cellular telephone 2054A, desktop computer 2054B, laptop computer 2054C, and/or automobile computer system 2054N may communicate. Nodes 2010 may communicate with one another. They may be grouped (not shown) physically or virtually, in one or more networks, such as Private, Community, Public, or Hybrid clouds as described hereinabove, or a combination thereof. This allows cloud computing environment 2050 to offer infrastructure, platforms and/or software as services for which a cloud consumer does not need to maintain resources on a local computing device. It is understood that the types of computing devices 2054A-N shown in FIG. 8 are intended to be illustrative only and that computing nodes 2010 and cloud computing environment 2050 can communicate with any type of computerized device over any type of network and/or network addressable connection (e.g., using a web browser).

Figure 9:
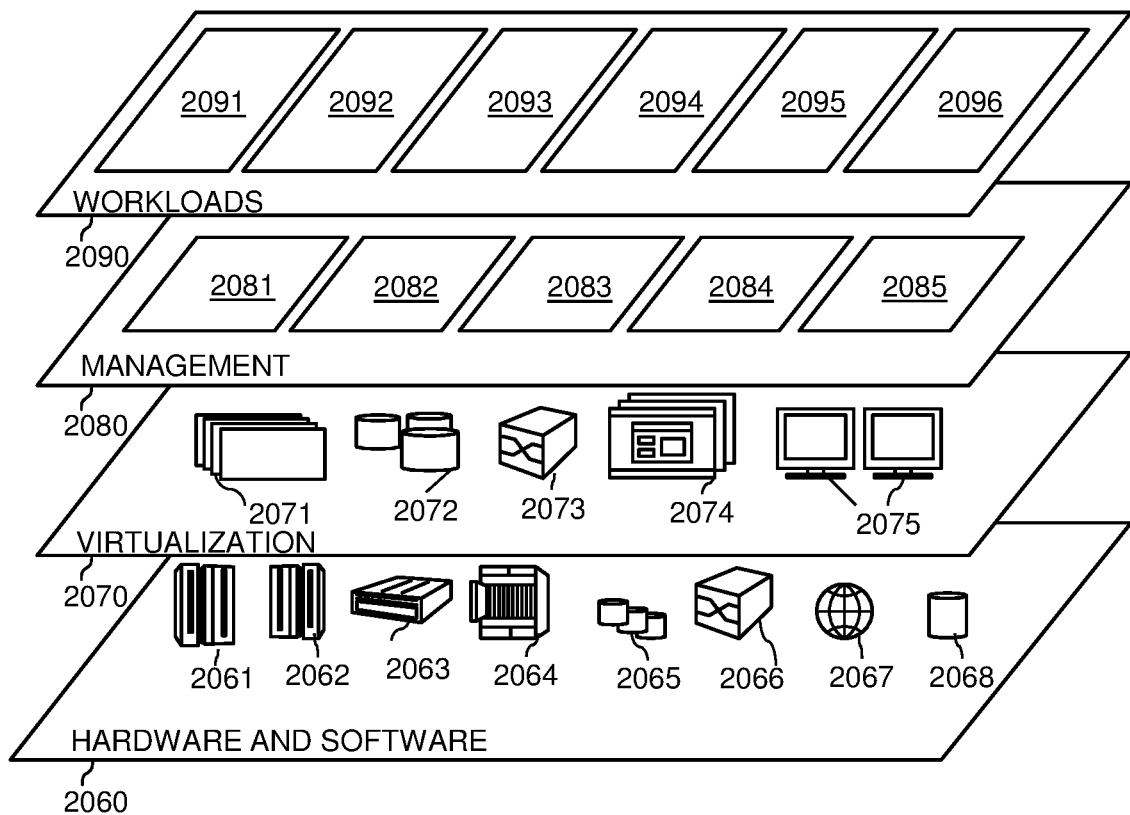
FIG. 9 is a block diagram depicting abstraction model layers according to an embodiment of the present invention.

Referring now to FIG. 9, a set of functional abstraction layers provided by cloud computing environment 2050 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 2060 includes hardware and software components. Examples of hardware components include: mainframes 2061; RISC (Reduced Instruction Set Computer) architecture based servers 2062; servers 2063; blade servers 2064; storage devices 2065; and networks and networking components 2066. In some embodiments, software components include network application server software 2067 and database software 2068.

Virtualization layer 2070 provides an abstraction layer from which the following examples of virtual entities may be provided: virtual servers 2071; virtual storage 2072; virtual networks 2073, including virtual private networks; virtual applications and operating systems 2074; and virtual clients 2075.

In one example, management layer 2080 may provide the functions described below. Resource provisioning 2081 provides dynamic procurement of computing resources and other resources that are utilized to perform tasks within the cloud computing environment. Metering and Pricing 2082 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 2083 provides access to the cloud computing environment for consumers and system administrators. Service level management 2084 provides cloud computing resource allocation and management such that required service levels are met. Service Level Agreement (SLA) planning and fulfillment 2085 provide pre-arrangement for, and procurement of, cloud computing resources for which a future requirement is anticipated in accordance with an SLA.

Workloads layer 2090 provides examples of functionality for which the cloud computing environment may be utilized. Examples of workloads and functions which may be provided from this layer include: mapping and navigation 2091; software development and lifecycle management 2092; virtual classroom education delivery 2093; data analytics processing 2094; transaction processing 2095; and data analysis of data received from a drone, wherein the data is captured in a drone enabled environmental having drone enabled testing of soil for ecological decision making 2096.

What is claimed is:

1. A computer-implemented method for capturing data in a drone enabled environment for testing soil and ecological decision making, comprising:

initiating, using a computer, collection of data from multiple sources using a drone, the data regarding information about soil at a specified soil location, in response to the drone flying over air space of a physical or geographical location respective to the soil location and/or landing at the soil location;

receiving, using the computer, soil data, as part of the data, from the drone in response to testing the soil, the testing of the soil including conducting a ground conductivity test using two or more probes coupled to respective landing pads of the drone, and positioning the drone over the soil location such that the two or more probes contact the soil;

analyzing the data to determine a best location for seeding and growing a plant in the soil;

initiating, as part of the testing of the soil, physical contact of a probe into the soil, wherein the probe is frangible and breaks off the drone when physical resistance from the soil exceeds a stress threshold;

receiving additional soil data, as part of the data, from the probe including first stress data related to the probe breaking off in response to the physical resistance from the soil exceeding the stress threshold; and analyzing the additional data to determine a best location for seeding and growing a plant in the soil.

2. The method of claim 1, wherein the ground conductivity test uses four probes coupled to four landing pads of the drone, and the method further comprising:

initiating electrical measurements using the four probes including a multiplicity of resistance measurements using a set of possible combinations of the four probes; and receiving, using the computer, the electrical measurements from the drone as part of the soil data.

3. The method of claim 1, further comprising:

initiating, as part of the testing of the soil, physical contact of another probe on the soil, wherein the another probe is a ribbon-line electrode providing continual measurement data in response to being dragged along the soil; and analyzing the measurement data from the ribbon-line electrode to determine a best location for seeding and growing a plant in the soil.

4. The method of claim 3, further comprising:

receiving additional soil data, as part of the data, from the another probe including second stress data related to the another probe breaking off in response to physical resistance from the soil exceeding a stress threshold; and analyzing the additional soil data to determine a best location for seeding and growing a plant in the soil, in response to the receiving of the additional soil data.

5. The method of claim 1, further comprising:

initiating, as part of the testing of the soil, drilling into the soil, using a mini drill coupled to the drone;

receiving soil samples from the drilling when the drone returns to a home base;

generating soil sample data, as part of the data, from the soil samples; and analyzing the soil sample data to determine a best location for seeding and growing a plant in the soil.

6. The method of claim 1, wherein the conducting of the ground conductivity test uses four probes coupled to respective landing pads of the drone, and the drone is positioned over the soil location such that the four probes contact the soil; and the method further comprising:

initiating testing of the soil using resistance measurements between the four probes;

receiving, using the computer, the soil data, as part of the data, including the resistance measurements from the drone in response to the testing the soil using the four probes; and analyzing the data to determine a best location for seeding and growing a plant in the soil.

7. The method of claim 6, wherein the testing of the soil using the resistance measurements between the four probes includes determining an optimum resistance using vector algebra.

8. The method of claim 6, wherein the testing of the soil using the resistance measurements between the four probes includes using a mathematical combination of the four probes.

9. A system using a computer for capturing data in a drone enabled environment for testing soil and ecological decision making, which comprises:

a computer system comprising; a computer processor, a computer-readable storage medium, and program instructions stored on the computer-readable storage medium being executable by the processor, to cause the computer system to perform the following functions to;

initiate, using a computer, collection of data from multiple sources using a drone, the data regarding information about soil at a specified soil location, in response to the drone flying over air space of a physical or geographical location respective to the soil location and/or landing at the soil location;

receive, using the computer, soil data, as part of the data, from the drone in response to testing the soil, the testing of the soil including conducting a ground conductivity test using two or more probes coupled to respective landing pads of the drone, and positioning the drone over the soil location such that the two or more probes contact the soil;

analyze the data to determine a best location for seeding and growing a plant in the soil;

initiate, as part of the testing of the soil, physical contact of a probe into the soil, wherein the probe is frangible and breaks off the drone when physical resistance from the soil exceeds a stress threshold;

receive additional soil data, as part of the data, from the probe including stress data related to the probe breaking off in response to the physical resistance from the soil exceeding the stress threshold; and analyze the additional data to determine a best location for seeding and growing a plant in the soil.

10. The system of claim 9, wherein the ground conductivity test uses four probes coupled to four landing pads of the drone, and the system further comprising the functions to:

initiate electrical measurements using the four probes including a multiplicity of resistance measurements using a set of possible combinations of the four probes; and receive, using the computer, the electrical measurements from the drone as part of the soil data.

11. The system of claim 9, further comprising the functions to:

initiate, as part of the testing of the soil, physical contact of another probe on the soil, wherein the another probe is a ribbon-line electrode providing continual measurement data in response to being dragged along the soil; and analyze the measurement data from the ribbon-line electrode to determine a best location for seeding and growing a plant in the soil.

12. The system of claim 11, further comprising the following functions to:
  receive additional soil data, as part of the data, from the another probe including stress data related to the another probe breaking off in response to physical resistance from the soil exceeding a stress threshold; and
  analyze the additional soil data to determine a best location for seeding and growing a plant in the soil, in response to the receiving of the additional soil data.

13. The system of claim 9, further comprising the following functions to:
  initiate, as part of the testing of the soil, drilling into the soil, using a mini drill coupled to the drone;
  receive soil samples from the drilling when the drone returns to a home base;
  generate soil sample data, as part of the data, from the soil samples; and
  analyze the soil sample data to determine a best location for seeding and growing a plant in the soil.

14. The system of claim 9, wherein the conducting of the ground conductivity test uses four probes coupled to respective landing pads of the drone, and the drone is positioned over the soil location such that the four probes contact the soil; and the method further comprising:
  initiating testing of the soil using resistance measurements between the four probes;
  receiving, using the computer, the soil data, as part of the data, including the resistance measurements from the drone in response to the testing the soil using the four probes; and
  analyzing the data to determine a best location for seeding and growing a plant in the soil.

15. The system of claim 14, wherein the testing of the soil using the resistance measurements between the four probes includes determining an optimum resistance using vector algebra.

16. The system of claim 14, wherein the testing of the soil using the resistance measurements between the four probes includes using a mathematical combination of the four probes.

17. A computer program product for capturing data in a drone enabled environment for testing soil and ecological decision making, the computer program product comprising a computer readable storage medium having program instructions embodied therewith, the program instructions executable by a computer to cause the computer to perform functions, by the computer, comprising the functions to:
  initiate, using a computer, collection of data from multiple sources using a drone, the data regarding information about soil at a specified soil location, in response to the drone flying over air space of a physical or geographical location respective to the soil location and/or landing at the soil location;
  receive, using the computer, soil data, as part of the data, from the drone in response to testing the soil, the testing of the soil including conducting a ground conductivity test using two or more probes coupled to respective landing pads of the drone, and positioning the drone over the soil location such that the two or more probes contact the soil;
  analyze the data to determine a best location for seeding and growing a plant in the soil;
  initiate, as part of the testing of the soil, physical contact of a probe into the soil, wherein the probe is frangible and breaks off the drone when physical resistance from the soil exceeds a stress threshold;
  receive additional soil data, as part of the data, from the probe including stress data related to the probe breaking off in response to the physical resistance from the soil exceeding the stress threshold; and
  analyze the additional data to determine a best location for seeding and growing a plant in the soil.

18. The computer program product of claim 17, wherein the ground conductivity test uses four probes coupled to four landing pads of the drone, and the computer program product further comprising the functions to:
  initiate electrical measurements using the four probes including a multiplicity of resistance measurements using a set of possible combinations of the four probes; and
  receive, using the computer, the electrical measurements from the drone as part of the soil data.

19. A computer-implemented method for capturing data in a drone enabled environment for testing soil and ecological decision making, comprising:
  initiating, using a computer, collection of data from multiple sources using a drone, the data regarding information about soil at a specified soil location, in response to the drone flying over air space of a physical or geographical location respective to the soil location and/or landing at the soil location;
  receiving, using the computer, soil data, as part of the data, from the drone in response to testing the soil, the testing of the soil including conducting a ground conductivity test using two or more probes coupled to respective landing pads of the drone, and positioning the drone over the soil location such that the two or more probes contact the soil;
  analyzing the data to determine a best location for seeding and growing a plant in the soil;
  initiating, as part of the testing of the soil, physical contact of another probe on the soil, wherein the another probe is a ribbon-line electrode providing continual measurement data in response to being dragged along the soil;
  analyzing the measurement data from the ribbon-line electrode to determine a best location for seeding and growing a plant in the soil;
  receiving additional soil data, as part of the data, from the another probe including second stress data related to the another probe breaking off in response to physical resistance from the soil exceeding a stress threshold; and
  analyzing the additional soil data to determine a best location for seeding and growing a plant in the soil, in response to the receiving of the additional soil data.

20. A system using a computer for capturing data in a drone enabled environment for testing soil and ecological decision making, which comprises:
  a computer system comprising; a computer processor, a computer-readable storage medium, and program instructions stored on the computer-readable storage medium being executable by the processor, to cause the computer system to perform the following functions to;
  initiate, using a computer, collection of data from multiple sources using a drone, the data regarding information about soil at a specified soil location, in response to the drone flying over air space of a physical or geographical location respective to the soil location and/or landing at the soil location;
  receive, using the computer, soil data, as part of the data, from the drone in response to testing the soil, the testing of the soil including conducting a ground conductivity test using two or more probes coupled to respective landing pads of the drone, and positioning the drone over the soil location such that the two or more probes contact the soil;
analyze the data to determine a best location for seeding and growing a plant in the soil;
initiate, as part of the testing of the soil, physical contact of another probe on the soil, wherein the another probe is a ribbon-line electrode providing continual measurement data in response to being dragged along the soil;
analyze the measurement data from the ribbon-line electrode to determine a best location for seeding and growing a plant in the soil;
receive additional soil data, as part of the data, from the another probe including stress data related to the another probe breaking off in response to physical resistance from the soil exceeding a stress threshold; and
analyze the additional soil data to determine a best location for seeding and growing a plant in the soil, in response to the receiving of the additional soil data.

* * * * *